United States Patent [19]

Carr

[11] Patent Number: 4,774,961
[45] Date of Patent: Oct. 4, 1988

[54] MULTIPLE ANTENNAE BREAST SCREENING SYSTEM

[75] Inventor: Kenneth A. Carr, Harvard, Mass.

[73] Assignee: M/A Com, Inc., Burlington, Mass.

[21] Appl. No.: 920,295

[22] Filed: Oct. 24, 1986

Related U.S. Application Data

[63] Continuation-in-part of Ser. No. 795,976, Nov. 7, 1985, abandoned.

[51] Int. Cl.⁴ .............................................. A61B 5/00
[52] U.S. Cl. ..................................... 128/736; 128/804
[58] Field of Search .................... 128/736, 804, 664.5, 128/660

[56] References Cited

U.S. PATENT DOCUMENTS

| | | | |
|---|---|---|---|
| 3,699,813 | 10/1972 | Lamb | 128/736 |
| 4,212,306 | 7/1980 | Mahmud | 128/665 |
| 4,275,741 | 6/1981 | Edrich | 128/736 X |
| 4,286,602 | 9/1981 | Guy | 128/665 |
| 4,310,003 | 1/1982 | Schlager | 128/736 |
| 4,346,716 | 8/1982 | Carr | 128/804 X |
| 4,524,779 | 6/1985 | Brown, Jr. | 128/736 |
| 4,570,638 | 2/1986 | Stoddart et al. | 128/665 |
| 4,583,869 | 4/1986 | Chive et al. | 128/736 X |

Primary Examiner—Kyle L. Howell
Assistant Examiner—Angela D. Sykes
Attorney, Agent, or Firm—Wolf, Greenfield & Sacks

[57] ABSTRACT

A method and apparatus for cancerous tumor detection employing a plurality of microwave antennae supported in an array conforming substantially in size to the breast that is being screened. In one embodiment of the invention a single array is used and another embodiment for larger breasts a pair of arrays are used. A microwave radiometer is used for detecting temperature readings corresponding respectively to the breast temperature at sites underlying the receiving antennae. Also, in accordance with the invention compression is employed so as to reduce tissue thickness enabling far more rapid reading of antenna sites.

31 Claims, 20 Drawing Sheets

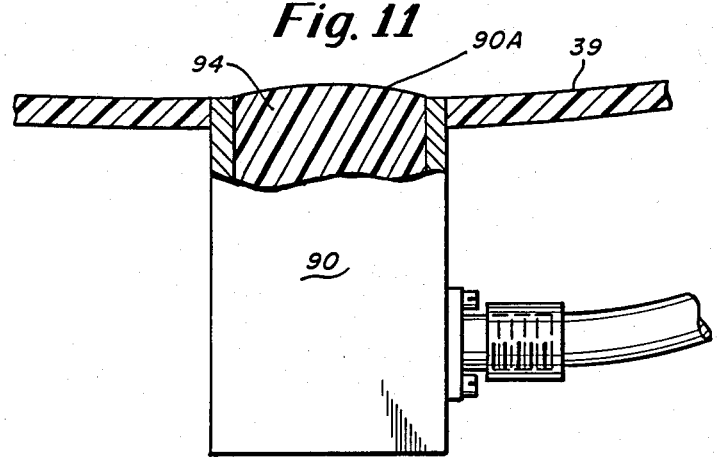
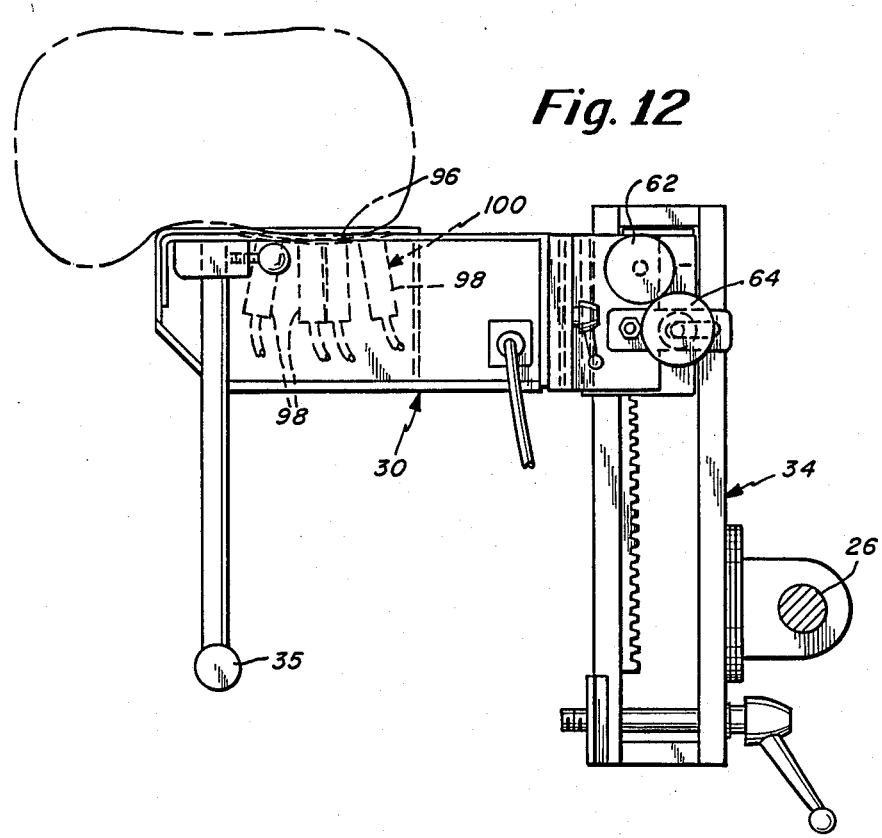

LEFT SIDE — AP (SMALL)

RIGHT SIDE — AP (SMALL)

LEFT SIDE — CRANIO-CAUDAD   (5 1/2 & 7 INCHES)

RIGHT SIDE — CRANIO-CAUDAD   (5 1/2 & 7 INCHES)

LEFT SIDE — OBLIQUE (5½ & 7 INCHES)

RIGHT SIDE — OBLIQUE (5½ & 7 INCHES)

LEFT SIDE — LATERAL (5½ & 7 INCHES)

RIGHT SIDE — LATERAL (5½ & 7 INCHES)

LEFT SIDE — CRANIO-CAUDAD    (9 INCHES)

RIGHT SIDE — CRANIO-CAUDAD    (9 INCHES)

LEFT SIDE — OBLIQUE (9 INCHES)

RIGHT SIDE — OBLIQUE (9 INCHES)

LEFT SIDE — LATERAL (9 INCHES)

RIGHT SIDE — LATERAL (9 INCHES)

MULTIPLE ANTENNAE BREAST SCREENING SYSTEM

RELATED APPLICATION

This is a continuation-in-part of application Ser. No. 795,976 filed Nov. 7, 1985, now abandoned.

BACKGROUND OF THE INVENTION

The present invention relates in general to an apparatus and associated method for the detection of cancerous tumors. More particularly, the invention relates to a system for the screening of cancerous tumors particularly female breast tumors. Even more particularly, the present invention relates to a microwave system for breast screening for locating tumors.

There is a continuing need for providing a reliable, noninvasive and nonhazardous technique for the detection of cancerous tumors especially breast tumors. One such technique is an infrared thermographic technique for cancer tumor detection, based on elevated temperatures often found in malignant tumors. This technique is noninvasive and nonhazardous but is of questionable accuracy. A more accurate techinque is mammography. One objection to the well known mammography technique is that it exposes the person to hazardous x-rays. With regard to infrared thermography, one of its drawbacks is its poor penetration through biological tissues, resulting in the measurement of only surface temperature.

Reference is also made to my U.S. Pat. No. 4,346,716 covering a microwave detection system for detection of cancerous tumors. This system employs a single detection antenna. If this system is employed for breast screening the examination time is far too long and is thus unacceptable. Furthermore, even though microwave techniques provide subsurface sensing, there is some limitation on the limit of depth detection.

In one prior system employing a single antenna this had to be mechanically positioned requiring approximately 1.5 minutes per site and a minimum of 9 positions per breast in order to provide acceptable coverage. This resulted in a time of examination of 30–40 minutes. Again, this is too long a period of time for practical purposes.

A further problem realized with the single antenna system is associated with the depth of the tumor, particularly in large breasts. It was found that there was a resultant high number of particularly false negative readings.

Accordingly, it is an object of the present invention to provide an improved method and apparatus for the detection of cancerous tumors, particularly breast tumors.

Another object of the present invention is to provide an improved breast screening technique employing microwave detection principles.

A further object of the present invention is to provide an improved microwave breast screening system employing multiple antennae which is instrumental in dramatically reducing the examination time.

Still another object of the presesnt invention is to provide an improved microwave breast screening system in which all antennae are stabilized at the same time eliminating thermal drift due to both patient and environmental changes.

A further object of the present invention is to provide a microwave breast screening system used in combination with breast compression so as to permit examination from opposite surfaces of the compressed breast tissue.

Still a further object of the present invention is to provide a microwave breast screening system having multiple antennae in which any given antenna thereof may be optimized for a given site. For example, the match of the nipple area of the breast is different from the surrounding tissue and thus the antenna element associated therewith can be optimized as to impedance match for that particular site.

SUMMARY OF THE INVENTION

To accomplish the foregoing and other objects, features and advantages of the invention, there is provided both an a means for supporting these antennae in an array that conforms substantially in size to the breast being screened. In addition to the use of a plurality of antennae, there is also provided in accordance with the invention means for compressing the breast so as to reduce the tissue thickness being examined. Means are provided coupled from the receiving antenna array for detecting the temperature readings corresponding, respectively, to the breast temperature at the sites underlining the receiving antennae. In accordance with one embodiment of the invention usable in particular for screening small breasts, the antennae are supported in a housing having a cupped surface at which the antennae are supported. The antenna array is substantially symmetric so as to provide multiple uniform breast coverage. In this embodiment of the invention as well as in the second embodiment to be described hereinafter each antenna has a domed end at the housing cupped surface so as to prevent air pockets between the housing and breasts. In the embodiment of the invention employing a single set of antennae the compression is carried out manually by the person being screened by virtue of providing a gripping bar associated with the apparatus, which gripping bar enables the person to firmly hold the antenna array against the breast. In this embodiment the cupped surface is supported substantially vertically.

In accordance with the second embodiment of the present invention, there are provided first and second sets of receiving antennae. In the embodiment disclosed herein there are six upper and six lower antennae. The means for supporting these antennae includes first and second housings each having a cupped surface at which the first and second sets of antennae are respectively supported. In this arrangement compression of one breast is followed by compression of the other breast. In this regard the first and second housings are commonly mounted with the associated cupped surfaces disposed in facing relative relationship with the first housing disposed substantially horizontal and in a fixed position and the second housing being supported over the first housing. In this embodiment the means for compression includes carriage means on a support member and means for operating the carriage means to bring the second housing toward the first housing to compress the breast between the housings. There is preferably provided a pivotal adjustment and a pivotal positioning of the second housing so that the second housing is at an angular tilted position relative to the first housing. This pivotal adjustment enables the operator of the apparatus to provide the proper amount of compression so that the antenna array is firmly disposed against the breast but at the same time does not make the compression uncomfortable to the person.

The breast compression that is used in accordance with the present invention has been found to provide many advantages. The compression reduces the material thickness and thus makes readings more accurate. With the dual housing arrangement there may then be a determination of depth by virtue of this compression because there will be examination from opposite surfaces of the compressed tissue. Furthermore, compression leads to tumor enhancement because of the reduced blood circulation thus reducing the temperature of the tissue surrounding the tumor with respect to the tumor tissue itself. The cancerous tissue tends to be hotter and by restricting the blood flow via compression this tends to enhance the temperature differential between the tumor site and the surrounding tissue.

In accordance with the associated method of the invention there are provided either a single or two pluralities of microwave receiving antennae. These are supported in either a single or two arrays with each array conforming substantially in size to the breast that is being screened. In either embodiment described herein, the breast is compressed so as to reduce tissue thickness that is being examined. Using a single set of antennae the breast is compressed inwardly under operation of the person being tested. In the second embodiment of the invention in which there are two sets of antenna arrays the breast is disposed between the array housings and the housings are brought together to cause compression. Compression of one breast is followed by compression of the second breast with common points on each breast being compared. In making these comparisons if there is a temperature differential between like sites on either breast then this may be an indication of a heated site area occasioned by the subsurface presence of a tumor.

BRIEF DESCRIPTION OF THE DRAWINGS

Numerous other objects, features and advantages of the invention should now become apparent upon a reding of the following detailed description taken in conjunction with the accompanying drawing, in which:

FIG. 11 is a further cross-sectional view showing further details as taken along line 11—11 of FIG. 10;

FIG. 12 is a plan view of the apparatus of the invention in the second embodiment of the invention in which the housing is substantially vertical and furthermore illustrating the compression of one breast against the antenna array;

DETAILED DESCRIPTION

Figure 1:
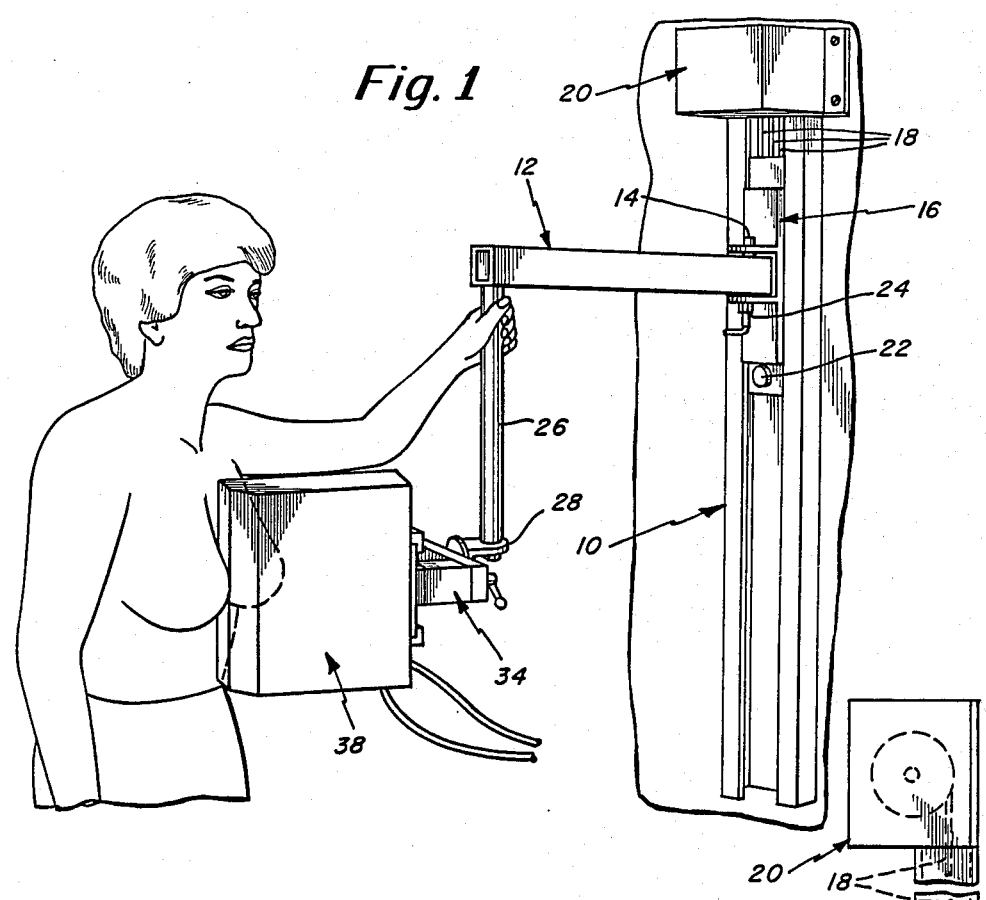
FIG. 1 is a perspective view illustrating a first embodiment of the present invention employing a double antenna housing with the housings in vertical adjacent position.
Figure 2:
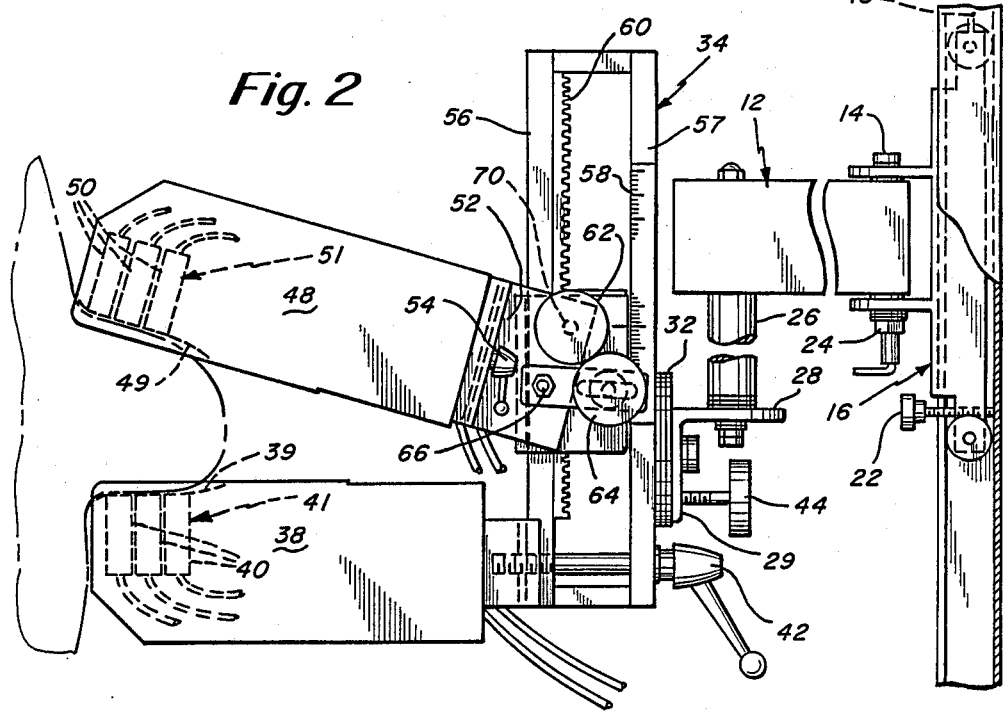
FIG. 2 is a side elevation view partially in cross-section illustrating this first embodiment of the invention employing a pair of antenna housings and furthermore illustrating the compression of the breast between these housings in substantially horizontal adjacent position.
Figure 3:
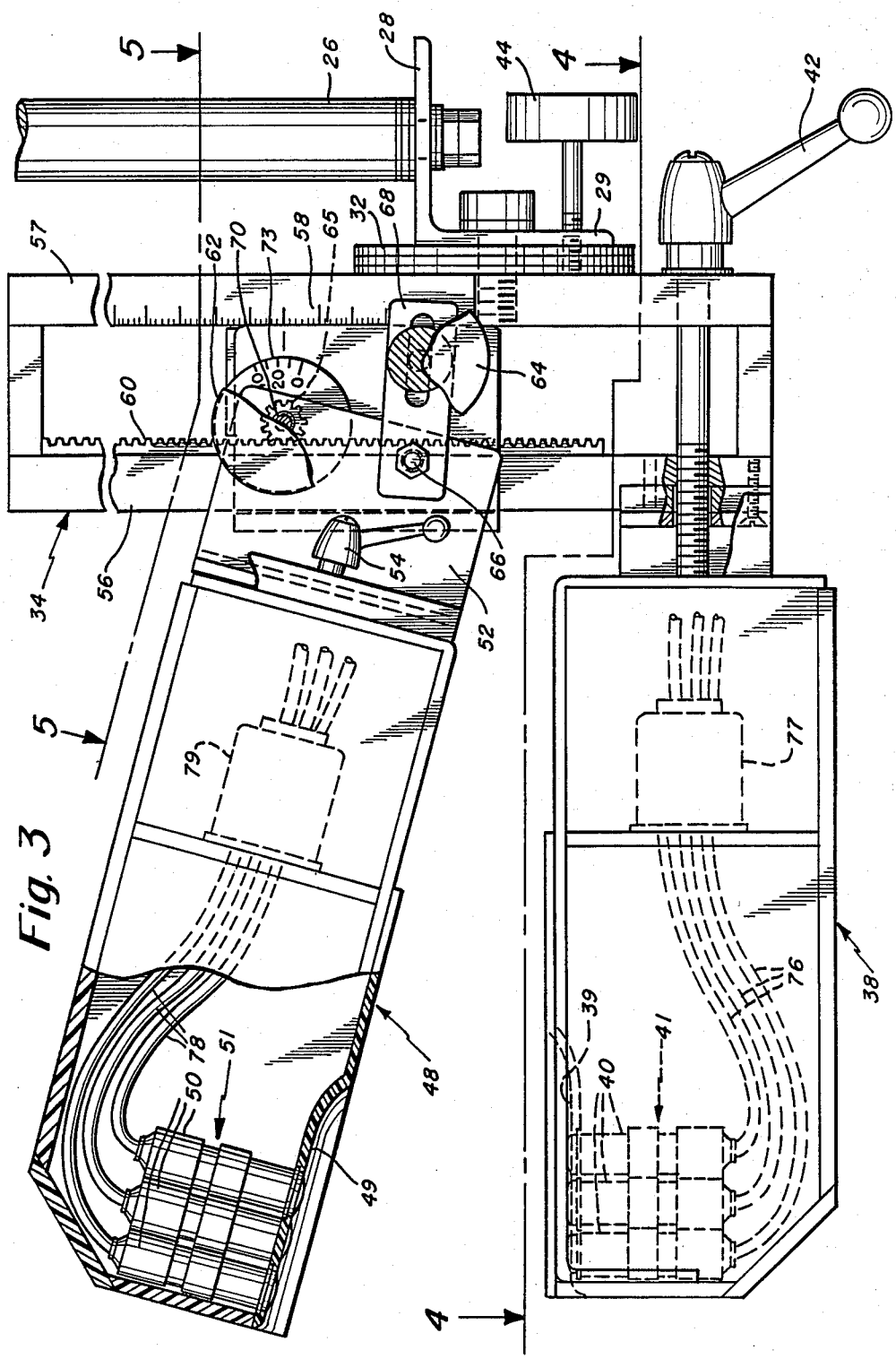
FIG. 3 is a further side elevation view partially in cross-section and illustrating further details in connection with the embodiment of FIG. 2.

Referring now to the drawings, there are described herein basically two different versions of detection apparatus for the microwave detection of breast tumors. In one version as noted in FIG. 12, there is the use of a single antenna housing. This is usable in particular with small breasts. For normal size to large breasts the dual housing arrangement is employed such as illustrated in FIGS. 1-3. In the dual housing arrangement the breast is compressed between the two housings as noted in dotted outline in FIG. 2. In either case in accordance with the invention there is provided a plurality of microwave receiving antennae. These antennae are used, as previously mentioned, in association with physical compression of the breast. The compression occurs in the second version as noted in FIG. 2. In the first version of the invention the compression occurs by virtue of the person being examined compressing the antenna array inwardly toward the chest against the breast.

The breast compression that is used in accordance with the present invention has been found to provide many advantages. The compression reduces the material thickness and thus makes readings more accurate. With the dual housing arrangement there may then be a determination of depth by virtue of this compression because there will be examination from opposite surfaces of the compressed tissue. Furthermore, compression leads to tumor enhancement because of the reduced blood circulation thus reducing the temperature of the tissue surrounding the tumor with respect to the tumor tissue itself. The cancerous tissue tends to be hotter and by restricting the blood flow via compression this tends to enhance the temperature differential between the tumor site and the surrounding tissue.

The use of multiple antennae provides improved performance. The individual antennae can be site-optimized. Also, data acquisition is possible thus dramatically reducing drift in both equipment and the patient. As indicated compression reduces tissue thickness and allows measurement from opposite surfaces of the breast. This enhances the ability to locate deep lesions. The results that are obtained can be carried out so that they can be readily compared to measurements taken by way of mammography techniques.

As indicated before, the multiple antenna approach results in improved performance due to site-optimized antennae. The multiple antennae reduce the examination time because all antennae are thermally matched simultaneously, allowing rapid data acquisition. Rapid data acquisition in turn eliminates or dramatically reduces drift due to environmental, equipment or patient conditions.

As mentioned previously, one of the advantages of the present invention is the reduction in examination time. However, it is further noted that with the use of both compression to reduce the tissue thickness and the ability to look from two opposing surfaces, this enables one to look deep into particularly large breasts. In addition, the use of multiple antennae allow site optimization of the antenna elements, such as might be necessary in the area of the nipple.

Now, with regard to the drawings and in particular to FIG. 1, there is illustrated the apparatus of the present invention which comprises a slide assembly 10 that may be secured to a wall in a room. This slide assembly 10 supports a beam 12 which is adapted to be maintained in a horizontal position as illustrated in FIG. 1. However, the beam 12 is pivotal about the axis 14. The beam 12 is carried in a vertically movable carriage 16 supported from cables 18 that extend from the counter balance assembly 20. The assembly 20 is at the top of the slide assembly 10. There is also provided a lock 22 that locks the carriage 16 in a desired vertical position. There is also provided a rotational lock 24 that locks the beam 12 in a certain horizontal rotational position. The operator of the apparatus can easily release the locks 22 and 24 to move the carriage 16 up and down and also to move the beam 12 in a horizontal plane. The beam 12 at its outer end supports the vertical post 26. The post 26 may be firmly secured at the end of the beam 12 and supports at its lower end bracket 28. Bracket 28 is an L-shaped bracket that is clearly illustrated in FIGS. 2 and 3. The interconnection between the bracket 28 and the post 26 permits pivotal frictional rotation between the bracket 28 and the post 26. This likewise permits rotational movement in a horizontal plane of the antenna housing 30.

The bracket 28 includes a leg 29 that is secured to the rotational pivot 32. The rotational pivot 32 is also secured to the main support member 34 of the apparatus. The rotational pivot 32 permits the support member 34 to rotate essentially in a vertical plane. In this regard, FIG. 1 shows the support member 34 in a horizontal position while FIG. 2 shows the support member 34 in a vertical position.

In FIGS. 1 and 2, double antenna housings are employed, but illustrated in different respective positions. In the instance illustrated in FIG. 1 the antenna housings 38, 48, (housing 48 being disposed behind housing 38) are both disposed in a vertical position corresponding to the left side lateral position illustrated in FIG. 19.

Hereinafter, in connection with FIGS. 12-14, there is an illustration of a single housing that is used. A single housing version of the invention is usable in particular with breasts of a size on the order of 4" or less.

For larger breasts that are defined herein as being in sizes of 5½", 7" or 9" the apparatus such as illustrated in FIGS. 1-3 are employed in which there are a pair of antenna housings. As far as the portion of the apparatus that supports the housings is concerned, the same basic construction is used in connection with the decription of FIGS. 1-3. Accordingly, like reference characters are of course used to identify like parts including the support member 34 illustrated herein. The antenna housing 38 is the lower most housing and includes a cupped surface 39 at which the antennae 40 are supported in an array 41. The housing 38 is supported at the very bottom end of the support member 34. There is provided a lower housing clamp 42 that locks the housing 38 in position. Above the clamp 42 is a further lock 44 that is used to lock the position of the rotation pivot 32.

With regard to the rotational pivot 32 it is noted that it is basically maintained in one of two different positions which are displaced 90° to each other. Again, in FIG. 1 it is shown in one position and in FIG. 2 it has been rotated 90° so that the support member 34 is in an upright position thus enabling the housings to be disposed on the support member in overlying relationship as illustrated in FIGS. 2 and 3.

The second antenna housing 48 is disposed in overlying relationship to the housing 38 and also has a cupped surface 49 at which the antennae 50 are supported. The antennae 50 are supported in an array 51.

The antenna housing 48 is also supported from the support member 34 but rather than being supported in a fixed position as is the housing 38, the housing 48 is supported both in the manner to pivot and also in a manner to move vertically relative to the housing 38. The housing 48 is supported from a U-shaped bracket 52 illustrated in a plan view in FIG. 5. The housing 48 is locked to the bracket 52 by means of the clamp 54. The housing 48 engages with the U-shaped bracket 52 and the sliding relationship therewith such as illustrated in FIG. 5.

As illustrated in FIG. 2, the support member 34 has slide pieces 56 and 57. The side piece 57 carries the scale 58. The scale 58 as illustrated in FIGS. 2, 3 and 5. The side piece 56 supports the rack 60.

Figure 5:
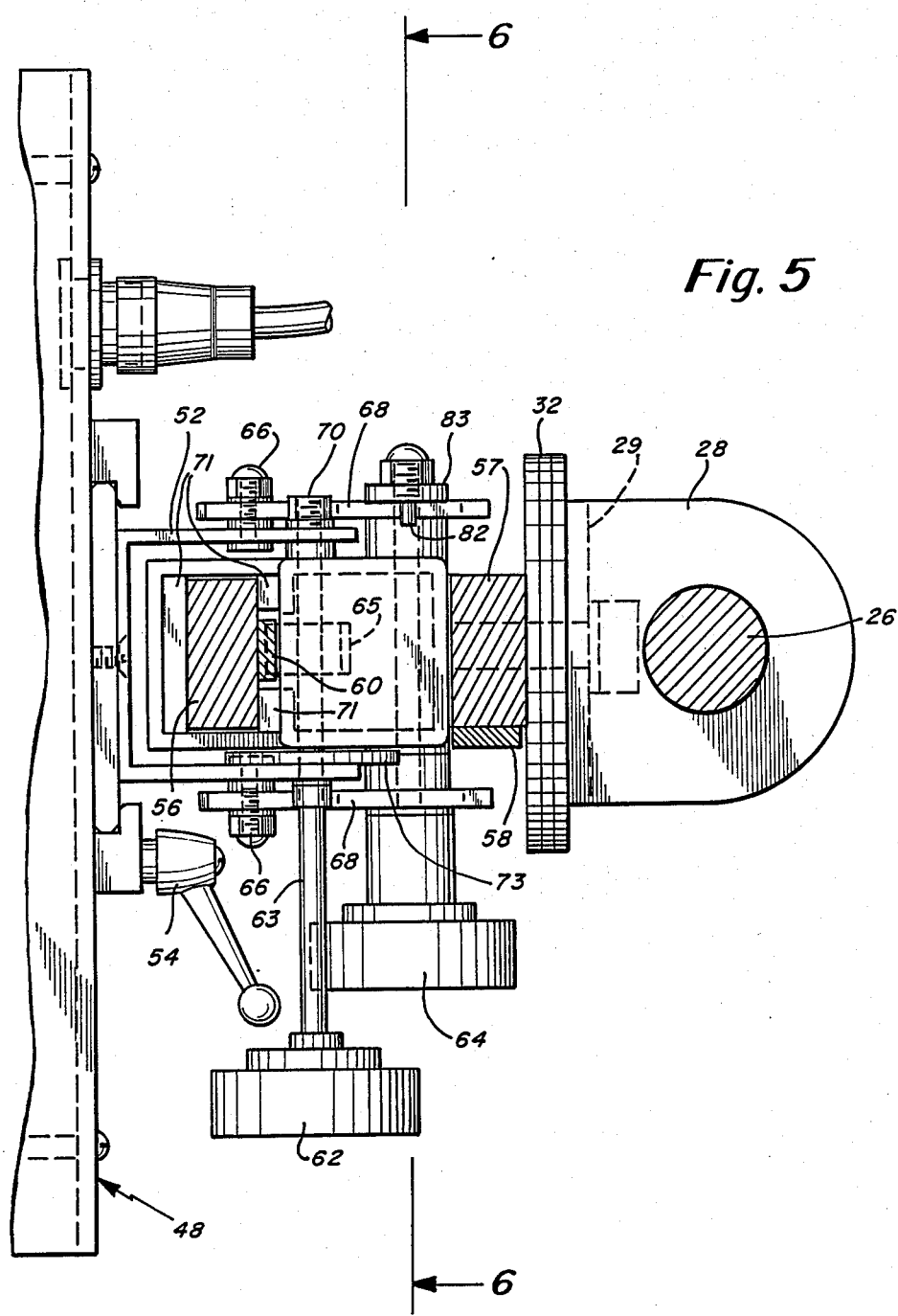
FIG. 5 is a partial cross-sectional plan view taken along line 5—5 of FIG. 3.

In FIGS. 2, 3 and 5 there are shown two control knobs associated with operation of the housing 48. One is the knob 62 and the other is the knob 64. The knob 62 is used to control the distance between the housings. This knob is attached to a shaft 63 that carries the pinion gear 65 that is adapted to engage with the rack 60. In this regard also note the cross-sectional view of FIG. 6 which shows the knob 62 connected to the pinion gear 65 which in turn is engaged with the rack 60.

The knob 64 clamps the rotational position of the antenna housing 48. This pivoting of the housing 48 is at the pivot 70. Knob 64 clamps the lock bars 68 against the frame to hold the antenna arrays in the proper angular position. As illustrated in FIGS. 3 and 5 there are also a pair of lock bars 68 associated with the pivot 66. In FIG. 5 the pivot for the housing 48 rotation is at 70.

Thus, the rack and pinion are engaged in order to move the housing 48 up and down and the knob 64 is used to clamp the housing 48 in a predetermined rotational position with the housing 48 rotating about a pivot axis as indicated at 70 in FIG. 5. FIG. 5 also shows the Teflon slides 71 disposed on either side of the rack 60 and also on the other side of the side piece 56. FIG. 5 furthermore illustrates the dial 73 which indicates rotation of the housing 48. In this regard also note the dial 73 in FIG. 3 indicating a degree of rotation of approximately 15°. The scale 58 is also illustrated in FIG. 3 and gives an indication of the displacement between the two housings. With regard to the dial 73 this is fixed to the U-shaped bracket 52 and thus rotates with the housing so as to indicate angular displacement of the housing 48.

FIG. 3 illustrates in dotted outline the antenna array 41 associated with housing 38 and also shows in cross-section the antenna array 51 associated with the housing 48. There are leads 76 coupling from each of the antennae 40 of array 41. These leads couple to a connector 77 and then there are output leads that couple from the housing 38. Similarly, there are leads 78 coupling from the antenna array 51 to a connector 79. From the connector there are leads that couple out of the movable antenna housing 48.

Figure 4:
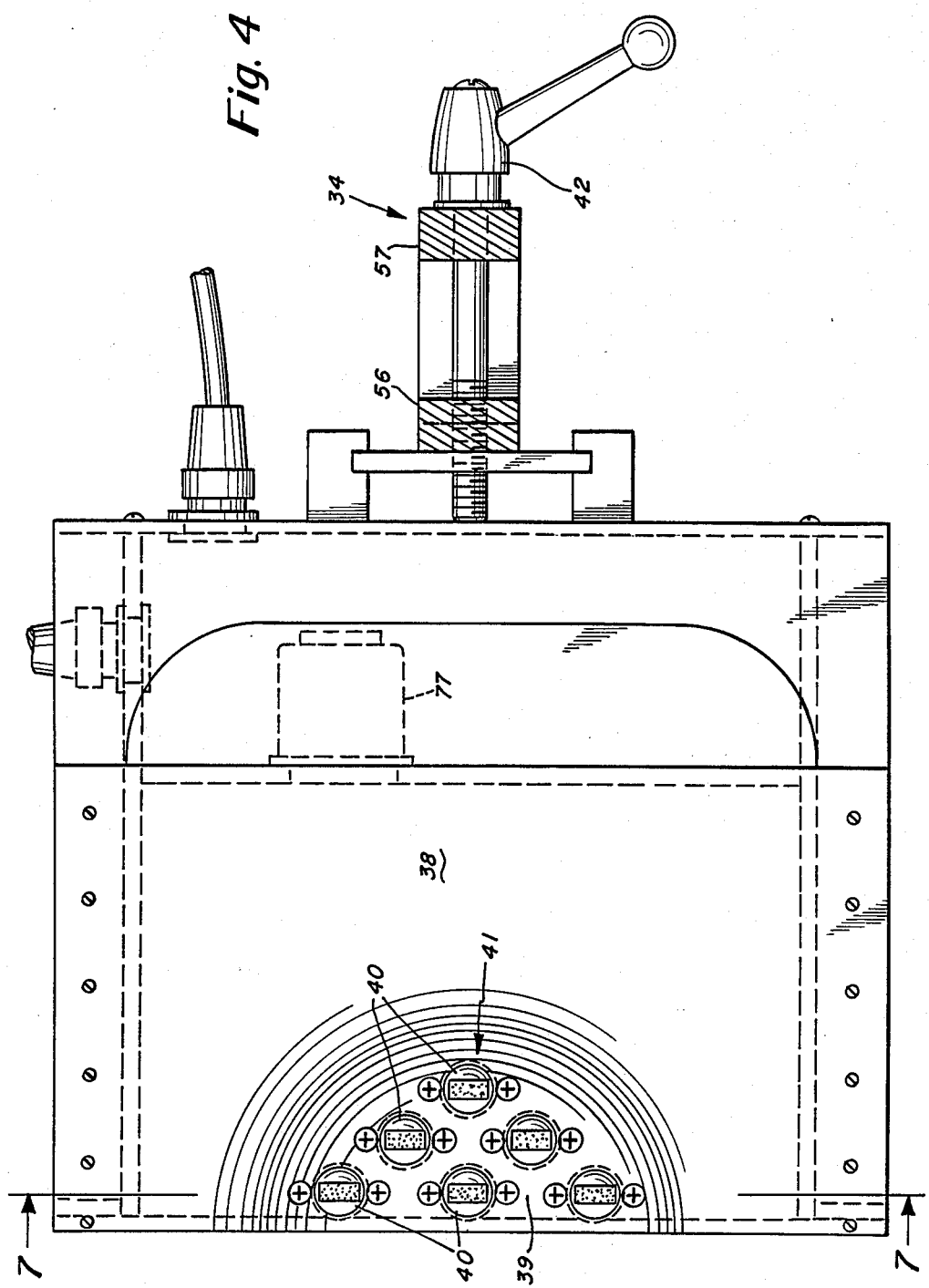
FIG. 4 is a partial cross-sectional plan view taken along line 4—4 of FIG. 3.

FIG. 4 is a plan view taken along line 4—4 of FIG. 3. This illustrates the particular placement of the antennae 40 in a triangular shaped array all disposed within the cupped surface 39. FIG. 4 also illustrates the coupling 77 and the coupling of leads out of the housing 48. FIG. 4 also illustrates the clamp 42 for clamping the housing 38 in position. In the particular embodiment illustrated as FIG. 4 the antenna array is for use with an intermediate size breast such as the aforementioned 5½" breast. The particular array has a lower most row of three antennae spaced apart, a second row of two antennae staggered in relationship to the first row and a third single antenna altogether making the triangular shape as aforementioned.

Figure 6:
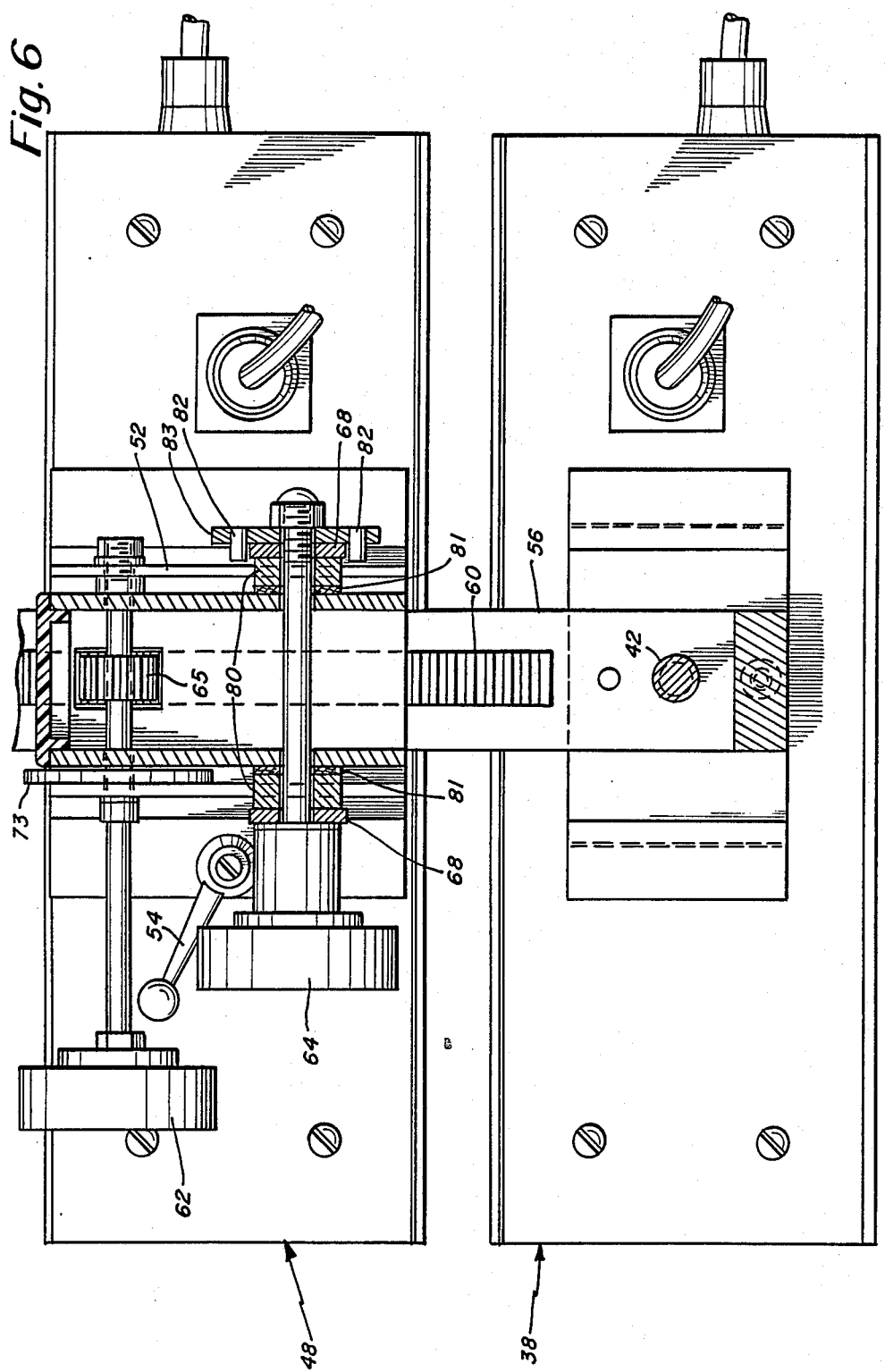
FIG. 6 is a partial cross-sectional rear elevation view taken along line 6—6 of FIG. 5.

Reference is now made to FIG. 6 which is a rear elevation view partially in cross-section showing further details of the apparatus illustrating the movable and rotational upper housing 48 and the fixed lower housing 38. There is illustrated the rotational clamp knob 64 and the knob 62 for setting the distance apart between the housings. FIG. 6 also illustrates the clamping or lock bars 68, spacers 80, and fiber washers 81. Pins 82 are disposed in association with the non-rotating washer 83.

Figure 7:
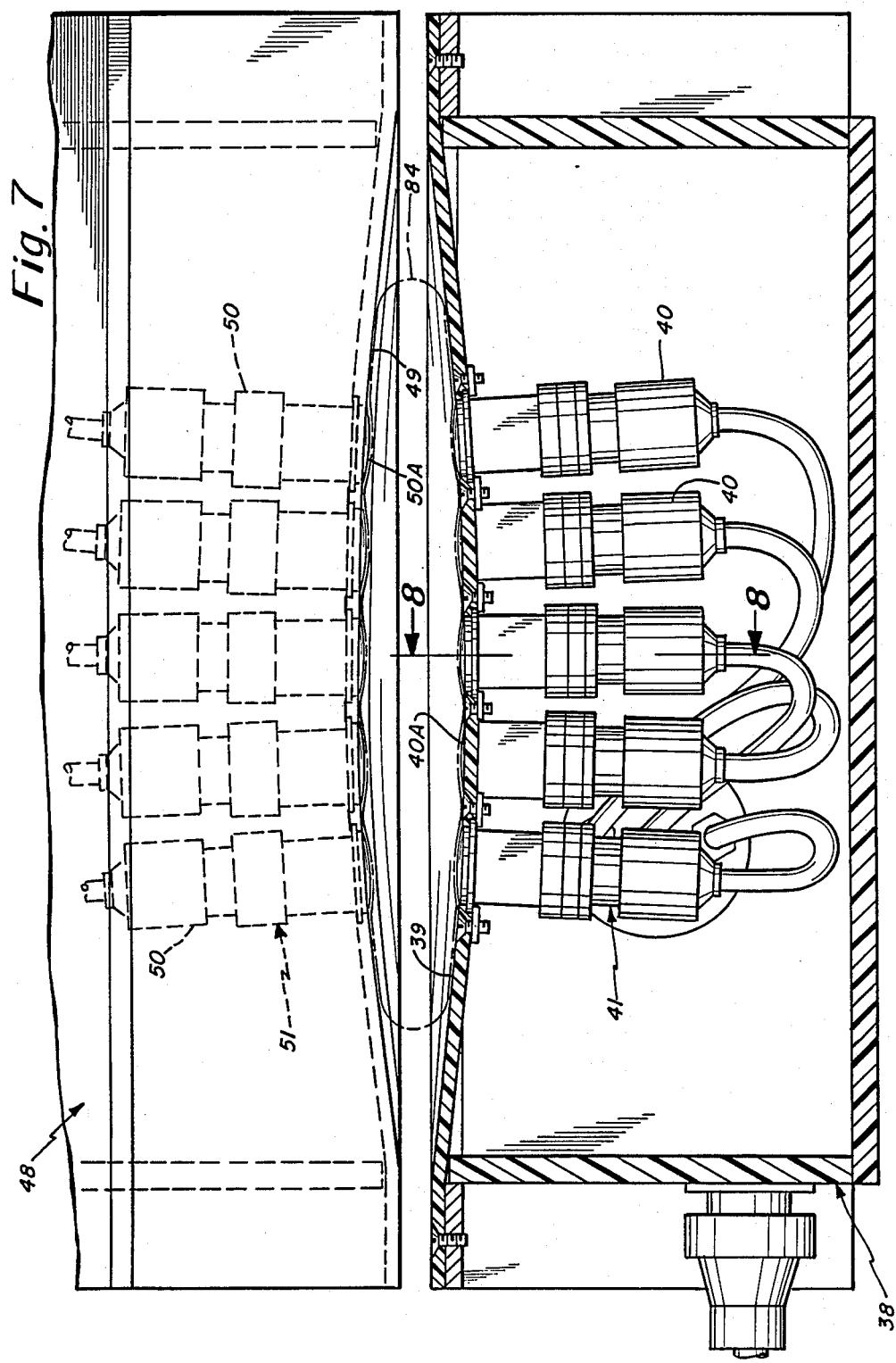
FIG. 7 is a partial cross sectional front elevation view taken along line 7—7 of FIG. 4.

Reference is now made to FIG. 7 that illustrates a cross-sectional view with the two housings in confronting relationship and which the cupped surfaces 39 and 49 are in facing relative relationship to each other. Therebetween there is shown a dotted outline a warming blanket 84 which is preferably used to warm the cupped surfaces prior to usage as will be described hereinafter. It is furthermore noted that each of the antennae 40 and each of the antennae 50 has a domed end 40A, 50A.

Figure 8:
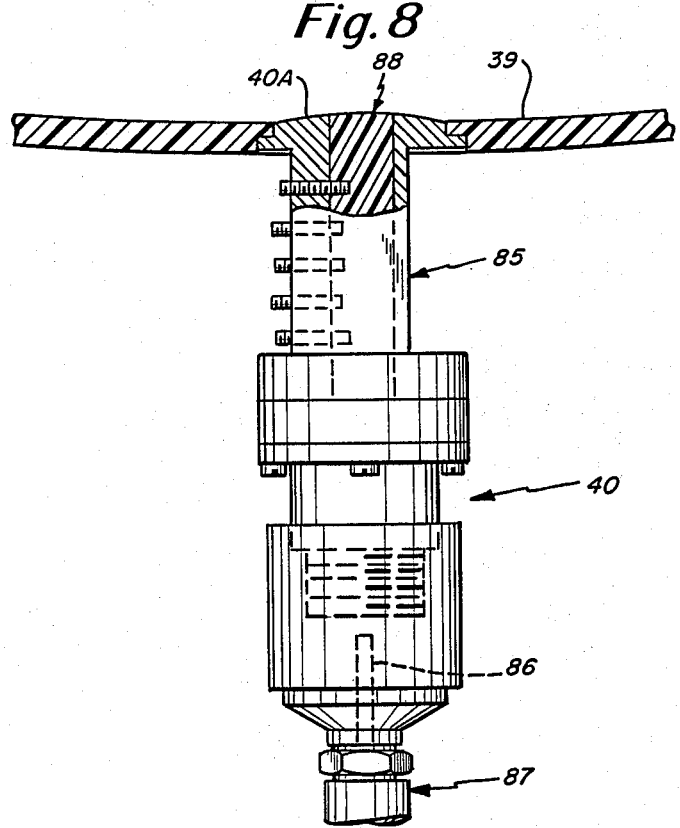
FIG. 8 is a cross-sectional view through one of the antennae as taken along line 8—8 of FIG. 7.

Reference is now made to FIG. 8 which is a cross-sectional view taken along line 8—8 of FIG. 7 showing further details of the antenna 40. This antenna is comprised of a section of waveguide 85 and a probe 86 coupling to the coaxial line 87. The waveguide 85 is preferably dielectrically filled as shown at 88 in FIG. 8. Also in FIG. 8 it is noted that there is clearly described the domed end 40A of the antenna.

Figure 9:
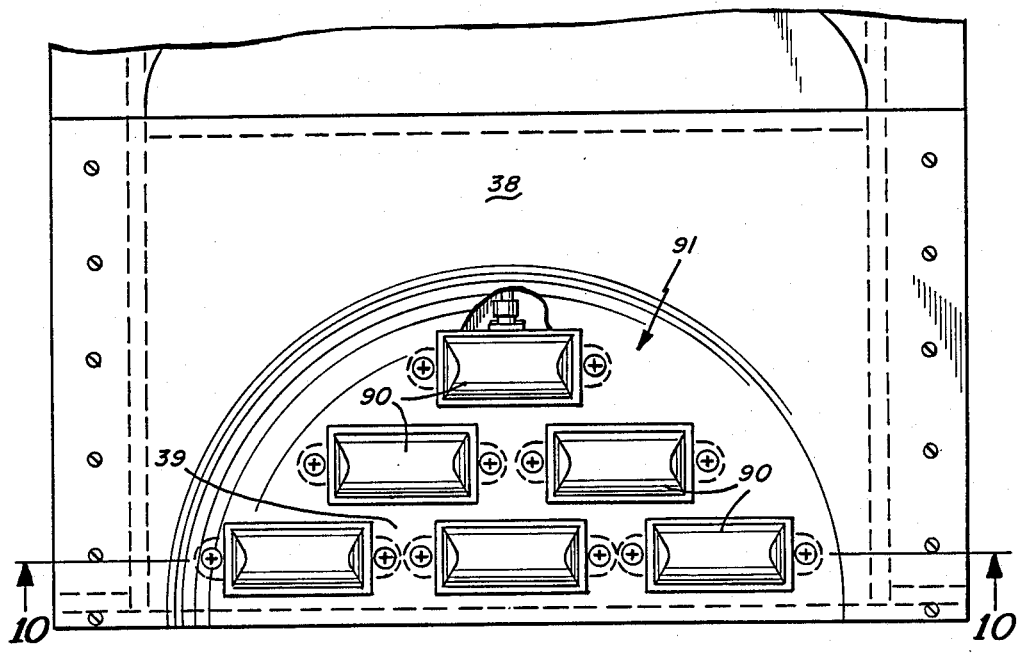
FIG. 9 is a plan view of an alternate antenna construction in accordance with the invention for use with larger breasts.

The embodiment of the invention illustrated in FIGS. 7 and 8 is used in connection with breast sizes of 5½" and 7". For a larger breast of 9" size then it is preferred to use the antenna form illustrated in FIGS. 9-11. It is noted that the breast diameter may be determined from previously available mammography data. FIG. 9 shows the series of antennae 90 disposed in an array 91 covering an area that matches the size of a relatively large breast identified as a 9" breast herein. As noted in FIG. 9, these antennae are disposed in the same general pattern as previously illustrated in FIG. 4 in a first row of three antennae, a second row of two antennae and then followed by a single antenna disposed in a staggered arrangement in a generally triangular array.

Figure 10:
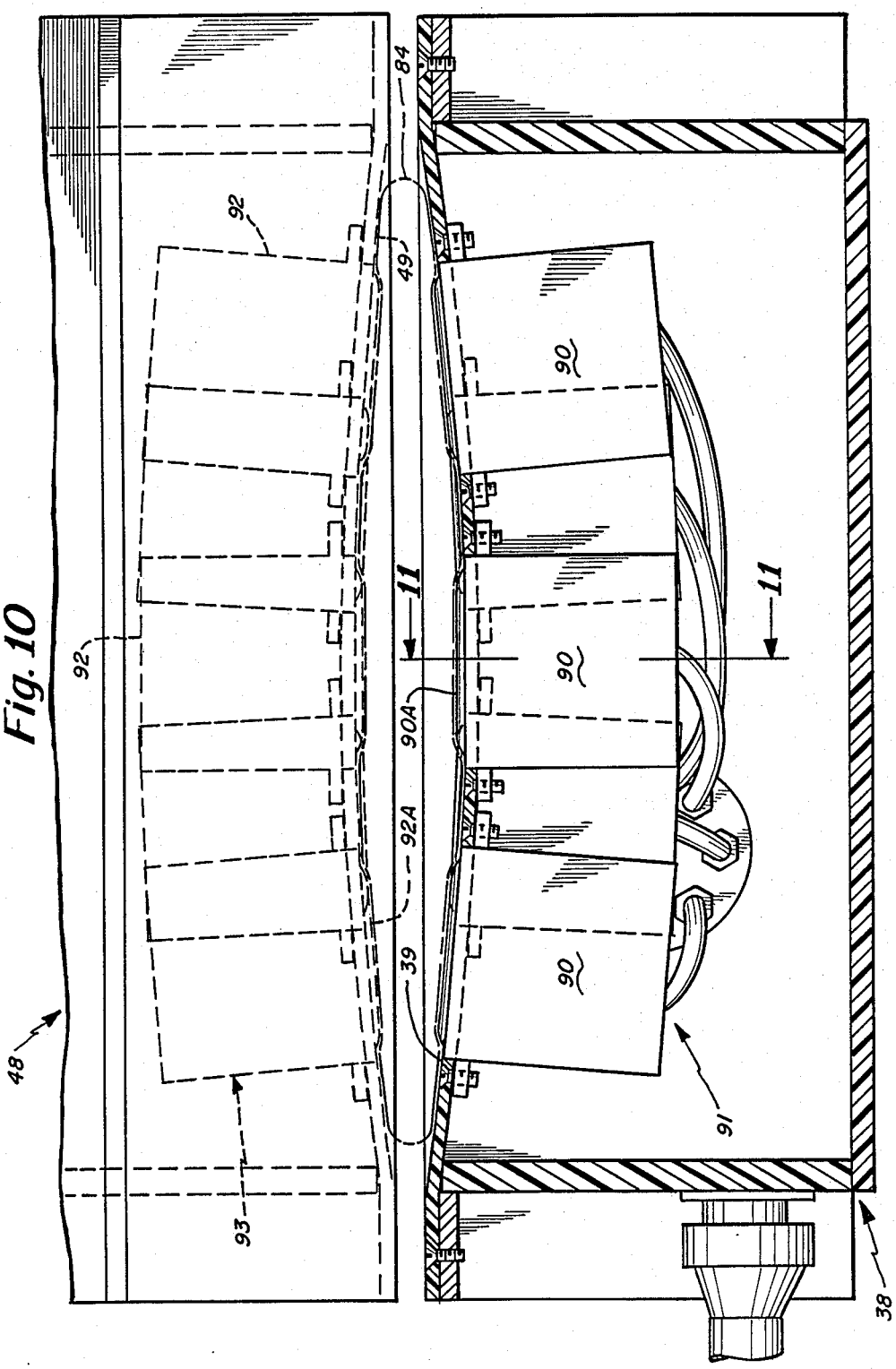
FIG. 10 is a cross-sectional view taken along line 10—10 of FIG. 9.

FIG. 10 is a cross-sectional view similar to that illustrated in FIG. 7 but for the large breast embodiment of the housing. Again, there is described in FIG. 10 the warming blanket 84 and dotted outline used to warm the ends of the antennae. The antennae 90 have domed ends 90A and the overlying antennae 92 have domed ends 92A. Again, these domed ends are for the purpose of preventing air pockets between the breast and the antennae. FIG. 10 also illustrates the cup surface 39 associated with housing 38 and the similar cup surface 49 associated with housing 48.

FIG. 11 is a cross-sectional view taken along line 11—11 of FIG. 10 showing some further detail of the microwave antenna illustrating in particular the cupped surface 39, domed end 90A and dielectric filling 94.

Thus, in this embodiment of the invention just described, there are two housings as in the embodiment illustrated in FIG. 8 each including 6 antennae of generally rectangular construction each comprising a section of waveguide and a probe for detecting signals from the waveguide. There is an array of antennae 91 associated with housing 38 and also an array 93 of antennae associated with the housing 48. Each of these arrays as noted comprises six antennae each with domed surfaces.

Reference has been made hereinbefore to the embodiment of the invention in which two housings are used such as in the different positions of FIG. 1 and 2. Mention has also been made of a single antenna housing 30 having associated therewith, handle 35 as referred to in FIG. 12. FIG. 12 also shows the outline of a breast 96. FIG. 12 also shows portions of the apparatus described in FIG. 1 including the vertical post 26, support member 34, and knobs 62 and 64. FIG. 12 also shows in dotted outline an array 100 of antennae 98.

Figure 13:
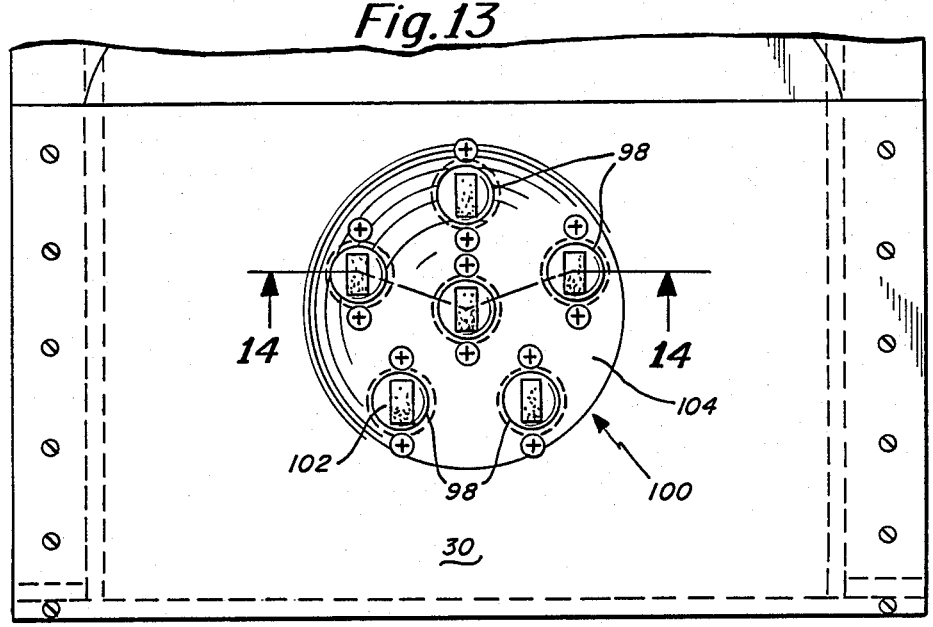
FIG. 13 is a plan view of the antenna array in the embodiment of FIG. 12.
Figure 14:
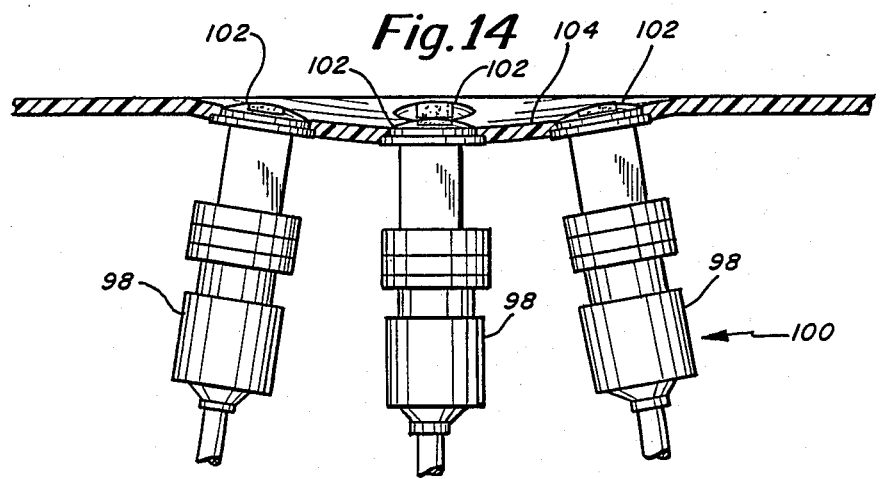
FIG. 14 is a cross-sectional view of the antenna array of FIG. 12 taken along line 14—14 of FIG. 13.

Reference is also made to FIGS. 13 and 14. FIG. 13 shows the housing 30 with the antenna array 100 comprised of six antennae 98. Each of the antennae 98 may be of the construction previously described such as shown in the detail of FIG. 8. The waveguide section thereof is preferably dielectrically filled and the waveguide section has a domed end 102. The array of six antennae are diposed in the circularly cupped surface 104.

FIG. 12 shows the placement of the breast compressed against the antenna array 100 this compression is brought about in this embodiment by virtue of the person being tested grasping the handle 35 and drawing the housing 30 against the breast to flatten the breast and compress it so as to cover the entire antenna array. As indicated previously this form of the invention is employed in particular with small breasts that may be too small to effectively compress between a pair of housings. Thus, instead a single housing is used with the associated handle 35 for providing compression directly against the breast.

Figure 15:
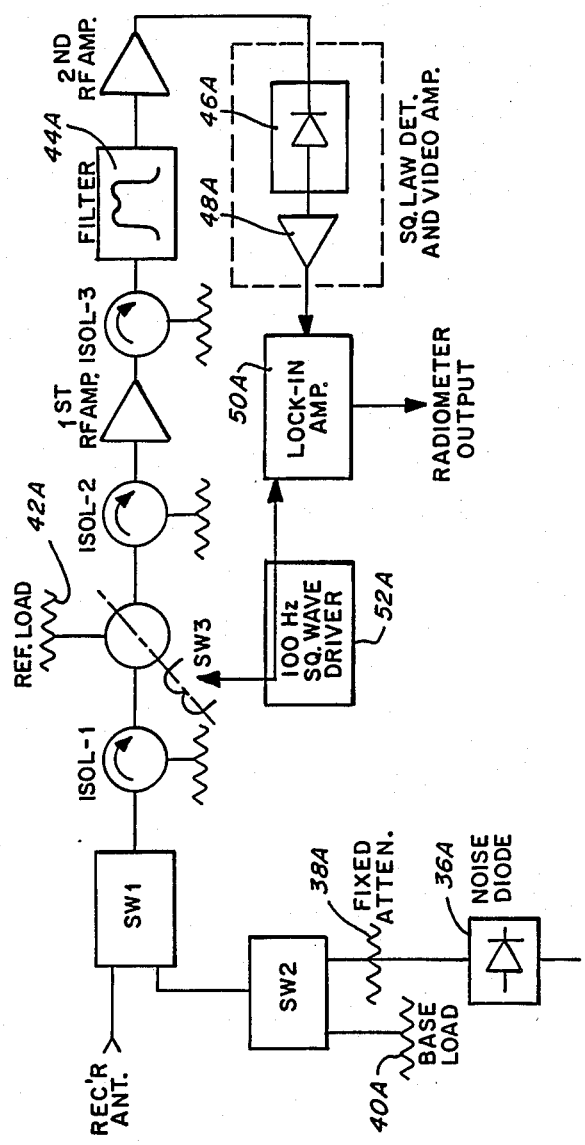
FIG. 15 is a schematic circuit diagram of a microwave radiometer employed in the system of this invention.

Now, reference is made to FIG. 15 which shows a schematic circuit diagram of a microwave radiometer that may be employed in the system of this invention for taking temperature measurements. Preferably, a single radiometer is employed and readings are taken in succession from each of the antennae as will be described hereinafter.

With regard to FIG. 15, there is illustrated an input to the switch SW1 from the receiver antenna such as from the antennae 40 or 50 as illustrated in FIGS. 2 and 3. The microwave radiometer that is depicted may be of the DICKE switch type. The radiometer design substantially reduces the effects of short term gain fluctuations in the radiometer. The receiver input is switched by means of a switch SW1 at a constant rate between the antenna and a constant temperature reference load. The switched, or modulated RF signal is therefore inserted at a point prior to RF amplification and as close to the antenna as possible; in turn, it is then amplified and coherently detected. The final output is proportional to the temperature difference between the antenna and the reference load.

In FIG. 15 a second switch SW2, referred to as a calibration switch, may also be employed. With this switch, the reference load as defined by the noise diode 36A and fixed attenuator 38A, is compared with a base load 40A rather than with the signal from the antenna. If the base load is equal in temperature with the reference load, the DC output of the radiometer is thus nulled to zero.

The radiometer described herein employs at least one low noise RF amplifier in conjunction with a simple single ended square law detector rather than the more complex superheterodyne which employs a local oscillator and IF amplifier. The square law detector of this arrangement minimizes the potential drift and noise associated with the superheterodyne approach. The conformance that comprises the radiometer are discussed in detail hereinafter.

With regard to the microwave radiometer schematic of FIG. 15, at its input there is shown the connection which is preferably by way of a coax cable from the receiver antenna (applicator aperture) to one input of switch SW1. This may be termed a calibration switch which is a solenoid-operated, mechanical single pole/double-throw switch used to disconnect the antenna and in its place connect the base load 40A by way of a second switch SW2. The switch SW1 has an isolation or switching radio, of greater than 60 dB with a corresponding insertion loss of less than 0.1 dB. The switch SW2 is used in the calibration circuit to disconnect the base load and to insert in its place the calibrated noise source as represented by the fixed attenuator 38A and the noise diode 36A referred to hereinafter.

As indicated in FIG. 15, there are three ferrite isolators used in the receiver path. These are identified as isolators ISOL-1, ISOL-2 and ISOL-3. The first isolator, is located between the calibration switch SW1 and the DICKE switch SW3. This isolator is used to terminate the output of the reference load when the DICKE switch is in the low loss state. In this state, the reference or base load is circulated in the direction of the antenna which, in this case, functions as a ferrite isolator. The isolator ISOL-1 employs a coaxial-to-waveguide transition. The insertion loss of this isolator and the transition is less than 0.2 dB, with a corresponding isolation of greater than 2.3 dB.

The second isolator ISOL-2 in FIG. 15, is disposed between the switch SW3 and the first stage RF amplifier to maintain a constant load match to this amplifier. Any reflections from the RF amplifier would therefore be terminated in the isolator. Again, this isolator, which is a waveguide isolator with a coax-to-waveguide transition, has an insertion loss of less than 0.2 dB with an isolation of greater than 23 dB.

There is also provided in FIG. 15 a third isolator ISOL-3 which is located between the output of the first RF amplifier and the bandpass filter 44A. The purpose of this particular isolator is to present a constant load match to the output stage of the first RF amplifier, and also to present a matched input to the bandpass filter 44A.

A switchable ferrite circulator, designated switch SW3 in FIG. 15, forms the load comparison, or DICKE switch, function. A ferrite device is preferred over a semiconductor approach primarily in view of the lower insertion loss, typically less than 0.3 dB, and elimination of noise generated by the semiconductor junction over and above the measured insertion loss.

Briefly, the device SW3 is a switchable ferrite junction circulator utilizing the remnant, or latching, characteristics of the ferrite material. The principle of latching action is as follows: Using the intrinsic properties of a hysteresis loop of a ferrite toroid, a transverse magnetic field is used across a portion of the ferrite exposed to an RF signal. The biasing field is actually the residual inductance of the ferrite toroid; therefore, the device needs no holding power and can be reversed in polarity using merely enough energy to overcome the natural coercive force of the toroid.

For the system of this invention, the latching circulator has been constructed in waveguide having a single ferrite element contained within the microwave circuit. The insertion loss is less than 0.3 dB, having isolation in excess of 20 dB.

The first-stage RF amplifier may be a four stage FET device constructed in microstrip with integrated biasing circuitry. The noise figure of the first amplifier (M/A Canada amplifier Model No. MC-2019) is 2.0 dB with a gain of 35 dB. The second RF amplifier Amplica Model No. 3441CS) has a noise figure of 2.6 dB, with an associated gain of 33 dB. In both instances, the noise figure includes the input ferrite isolator as depicted in FIG. 15. With the input and output VSWR at less than 1.5:1, the gain compression at signal levels of between $-55$ dbm to $-10$ dbm is less than 0.1 dB.

In FIG. 15 the filter 44A is a bandpass filter and the bandwidth of the microwave radiometer is basically determined by the bandpass characteristics of this filter. The filter is disposed after the first stage of RF amplification to minimize the impact of the insertion loss of the filter on the overall system performance. The filter characteristics are chosen to minimize possible interference due to nearby microwave communications or radar bands. The filter is preferably an 8-section bandpass filter constructed in stripline. The pass band loss is less than 3 dB and the bandwidth is approximately 500 MHz.

As indicated in FIG. 15, there are basically two loads provided, a base load 40 and a reference load 42A. The load design is coaxial, employing a stainless steel RF connector to provide thermal isolation between the load and the remainder of the system. The coaxial termination is contained within an insulated housing and utilizes an integrated heater and proportional control to maintain constant temperature. The absolute temperature of both the base and the reference loads is monitored and displayed on a digital temperature indicator (not shown).

The calibration circuit comprises a precision, solid state, noise source having an excess noise ratio, ENR of 33 dB. This allows noise to be injected into the receiver front end via the high isolation mechanical calibration switch. The output level of the noise source is reduced through the use of a precision calibrated pad (43.3 dB). This calibration circuit is shown in FIG. 15 as including a fixed attenuator 38A and the noise diode 36A.

The lock-in amplifier 50A shown in FIG. 15 enables the accurate measurement of signals contaminated by broad band noise, power line pickup, frequency drift or other sources of interference. It accomplishes this by means of an extremely narrow band detector which has the center of its pass band locked to the frequency of the signal to be measured. Because of the frequency lock and narrow bandwidth, large improvements in signal-to-noise ratio are achieved. This allows the signal of interest to be accurately measured, even in situations where it is completely masked by noise. In addition, the lock-in amplifier 50A provides the synchronous function associated with the DICKE switch; i.e., the unit supplies the 100 Hz reference clock frequency to drive the ferrite switch driver.

The system is provided, of course, with a power supply comprising two 12-volt 50 amp maintenance free, lead-acid batteries in series, fused at 10 amps per battery. The outputs from the battery assembly include 12 and 24 volts. These voltages are appropriately applied to the receiver and lock-in amplifier. There may also be provided a voltage converter and regulator. Status indicators may be employed for indicating operating voltages. The main operating switch may have three positions including an on position, an off position and a "charged" position. In the charged mode, a meter is used to monitor the charge current to the batteries which is limited to approximately 6 amps. With a 3-6 amp-hour discharge rate (a normal 12 hour operating mode), the recharge cycle is approximately 10-12 hours (overnight).

With the system of the present invention thermal drift is essentially eliminated. This is the case because all antennae are positioned concurrently and all readings taken substantially concurrently. Moreover, the antenna surface that the breast contacts is warmed so that the readings can be taken in say 1 minute to say 1.5 minutes rather than waiting a substantially longer time for proper temperature stabilization. It is preferred to warm the cupped surfaces 39 and 49 and of course the associated antenna domed ends to a temperature on the order of body temperature. This may be carried out by means of a warming pad as has been illustrated in the drawings. The preferred temperature that the cupped surfaces are raised to is in the range of 30° C.-34° C. This gets the surfaces that the breasts are going to come into contact with close to human skin temperature.

As indicated previously, in the embodiment employing a single antenna housing once the antennae are warmed the person being examined can themselves press the antenna array against the breast and readings can be taken in approximately 1 to 1.5 minutes. In the other embodiment of the invention that is more universally used, the lower antenna housing is fixed in position and the upper antenna housing moves downwardly and is capable of pivoting as clearly indicated in FIGS. 2 and 3 of this application to cause compression of the breast such as illustrated in dotted outline in FIG. 2. It has been found that the upper housing generally does not become horizontal but is instead moved to a position approximately as illustrated in FIG. 2 tilted at a slight angle usually in the range of 10°-35°. It has been found that it is preferred not to have the housings horizontal as this provides too much compression and discomfort regarding these breasts being examined. It is only necessary that the antenna array make good contact with the tissue and that there be no air gaps between the antenna and the tissue. It is also important that the antenna array be somewhat matched in size to the breast being examined so that all antennae are properly covered. Any air gaps will create a mismatch. Also, in accordance with the invention the domed antenna structure is important in assuring that air gaps or air pockets do not form.

Reference is now made to FIGS. 16A and 16B, 17A and 17B, 18A and 18B, 19A and 19B, 20A and 20B, 21A and 21B, and 22A and 22B in connection with a group of schematic diagrams that illustrate each of the different types of antenna arrays and the associated patterns for each breast. In this regard, FIGS. 16A and 16B relate to the single antenna housing version illustrated in FIGS. 1 and 12-14 of the invention. FIGS. 17A and 17B, 18A and 18B, and 19A and 19B show patterns associated with the dual antenna housings for 5½" and 7" breasts. Finally, FIGS. 20A and 20B, 21A and 21B, and 22A and 22B illustrate patterns in association with a 9" breast. In FIGS. 17A and 17B, 18A and 18B, 19A and 19B, 20A and 20B, 21A and 21B, and 22A and 22B the patterns are illustrated cranio-caudad oblique and lateral, respectively.

Figure 16A:
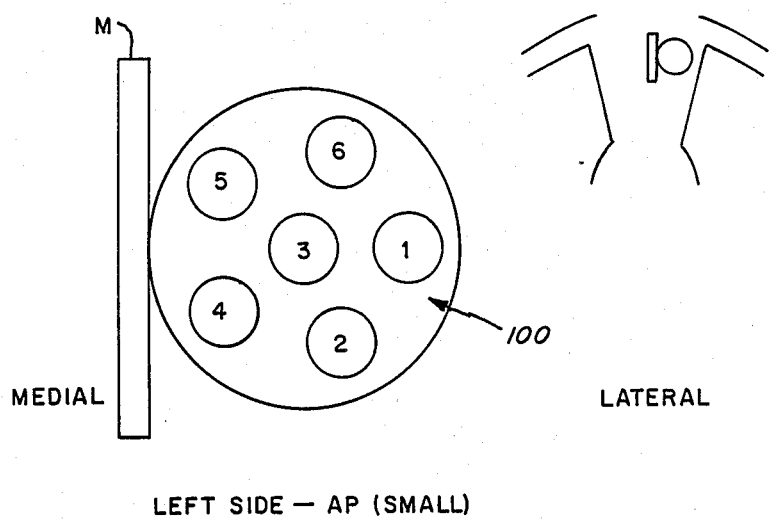
FIGS. 16A and 16B show the single housing antenna pattern.

FIG. 16A illustrates the antenna array 100 at the top for the left side and at the bottom for the right side. This is in connection with a relatively small size breast considered to be a 4" breast. Also note in FIG. 16A the medial markers M. Each of these arrays comprise six antennae identified as #1–#6. It is noted in the array illustrated in FIG. 16A that four of the antennae, #1, #2, #3 and #6 are grouped more closely together at the outside of the breast while #4 and #5 are grouped closer to the medial marker M.

Figure 16B:
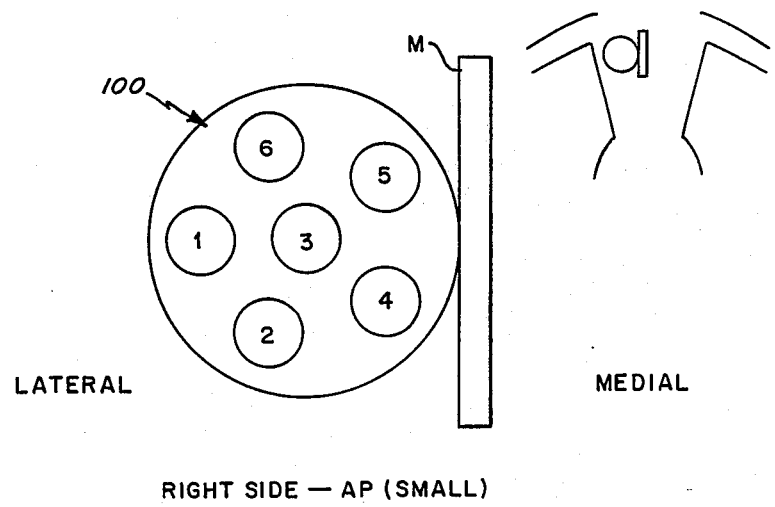

Now, it is noted that in FIGS. 16A and 16B the outermost antenna is #1 both with respect to the left breast and the right breast. This is so that the #1 readings are compared with comparisons being made at common points on each breast. For example, the right upper outer antenna #6 is compared with the left upper outer antenna #6. Because when the breast is compressed against the antenna array the antennae are actually in different positions depending upon whether it is the left breast or the right breast, information is fed into the system so that the proper comparisons are made of a common point on each breast. It may be, two separate housings 30 may even be employed one for the left breast and one for the right breast.

FIGS. 17A and 17B, 18A and 18B, and 19A and 19B illustrate schematically the antenna array placements for the dual arrays, these are the arrays previously referred to as arrays 41 and 51 in FIG. 7. Again, in, for example, FIGS. 17A and 17B the location #1 on the left side is compared with the location #1 on the right side. The position of FIGS. 17A and 17B relates to the position of housings of FIG. 2. Again, in connection with FIGS. 17A and 17B, 18A and 18B, and 19A and 19B it must be remembered that when one is observing both sides of the breast using six upper antennae and six lower antennae. Thus, the right outer upper antenna is compared with the same position on the left breast or in other words the left outer upper antenna. Because the breasts are inserted in the same direction between the antenna housings this means that the equipment must interpret whether a left breast or a right breast is being examined. It then senses the signals from the antennae in the proper manner so that the proper points are compared. For example, in FIGS. 17A and 17B it is noted that antenna #6 on the left side appears to be in line with antenna #1 on the right side. However, the electronics in the system interprets the readings differently so that the both #1 sites are compared between left and right sides.

Figure 17A:
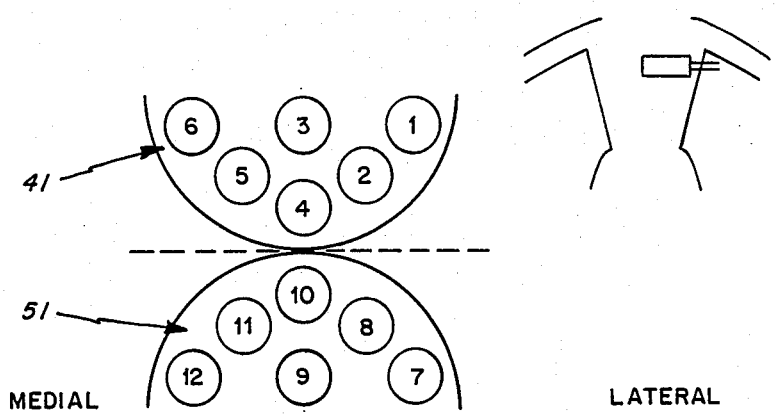
FIGS. 17A and 17B, 18A and 18B, and 19A and 19B show one version of the dual housing antenna patterns for different antenna placement positions.
Figure 17B:
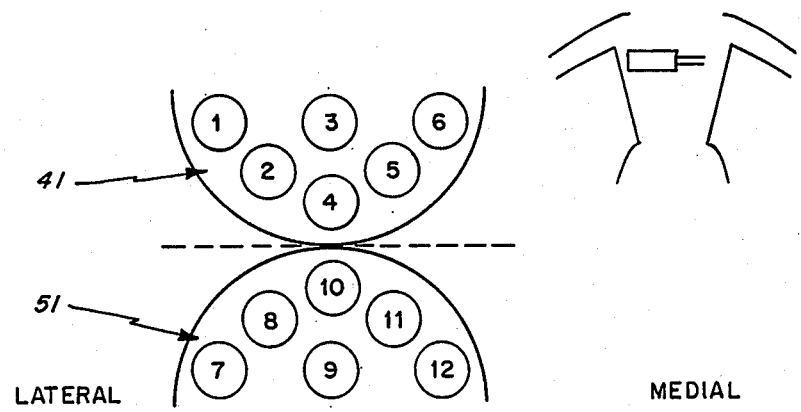
Figure 18A:
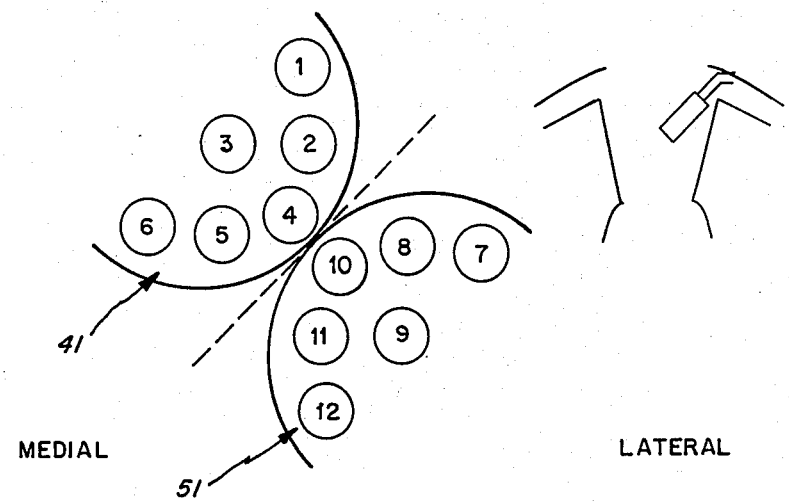
Figure 18B:
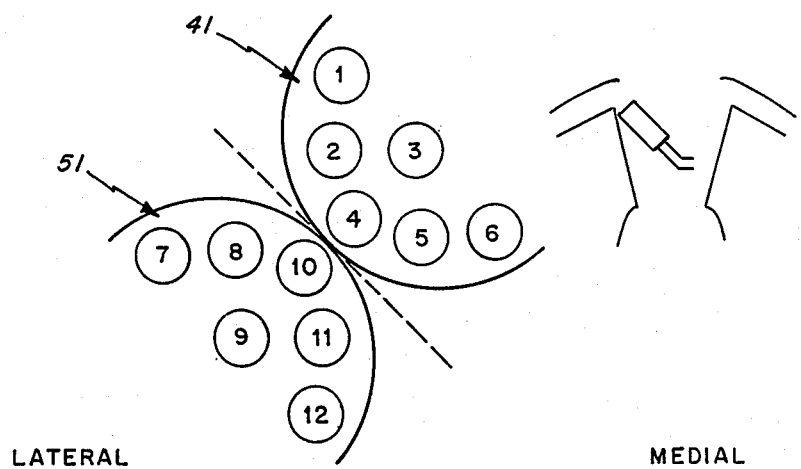
Figure 19A:
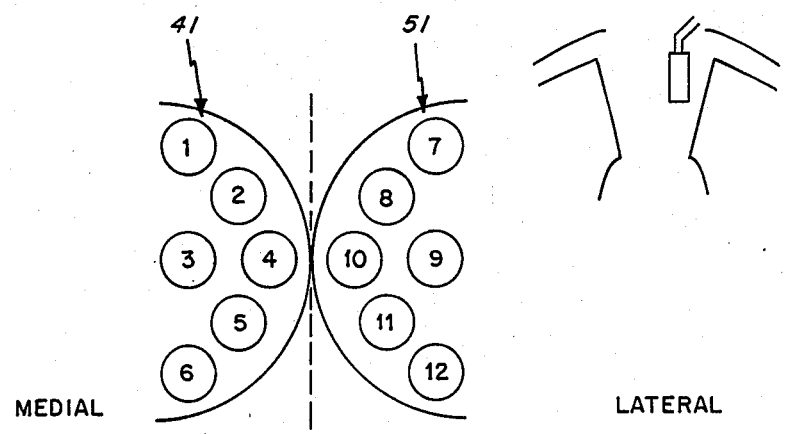
Figure 19B:
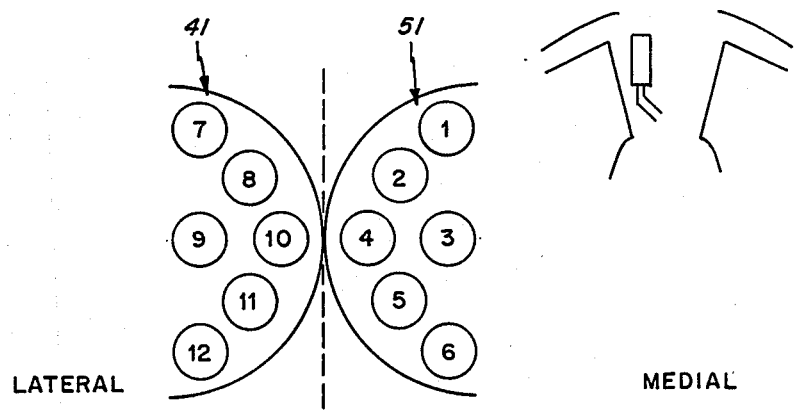

FIGS. 17A and 17B illustrate the detection and compression as being in the cranio-caudad direction. FIGS. 18A and 18B indicates the compression and sensing being at the oblique direction. In FIGS. 19A and 19B the sensing is done in the lateral position such as illustrated previously in FIG. 1.

FIGS. 20A and 20B, 21A and 21B, and 22A and 22B describes similar arrangements in connection with the embodiment of the invention illustrated in FIG. 10. This is for the larger breast employing arrays 91 and 93. Once again, comparisons are made between the same common points on each breast. For example, in FIGS. 20A and 20B the left upper outer antenna #1 is compared with the right outer upper antenna #1. When the breast is inserted into the position between the housings there may be in fact two different antennae that will be used for detecting these common points but the electronics interprets whether the left or right breast is being examined and then takes the appropriate reading from the appropriate antenna so that the common comparisons can take place.

Figure 20A:
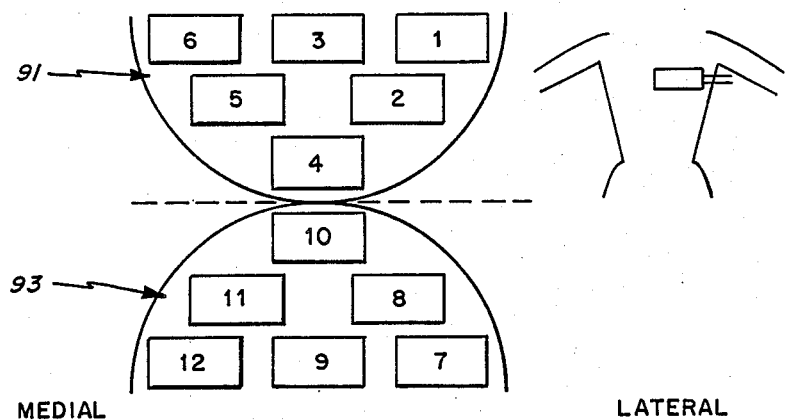
FIGS. 20A and 20B, 21A and 21B, and 22A and 22B show another version of the dual housing antenna patterns for different antenna placement positions.
Figure 20B:
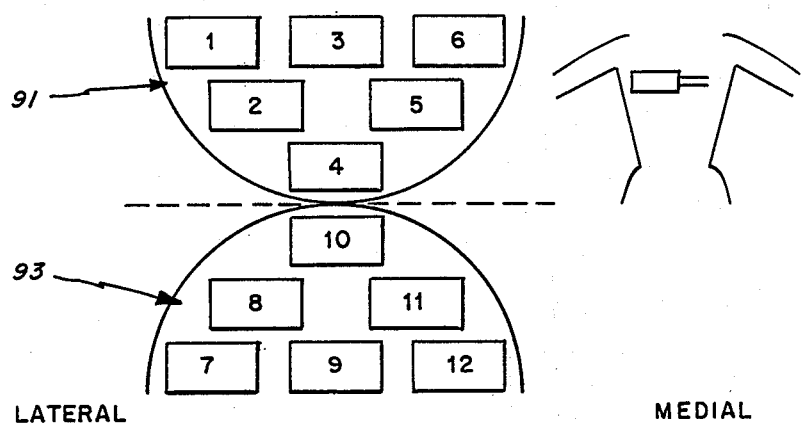
Figure 21A:
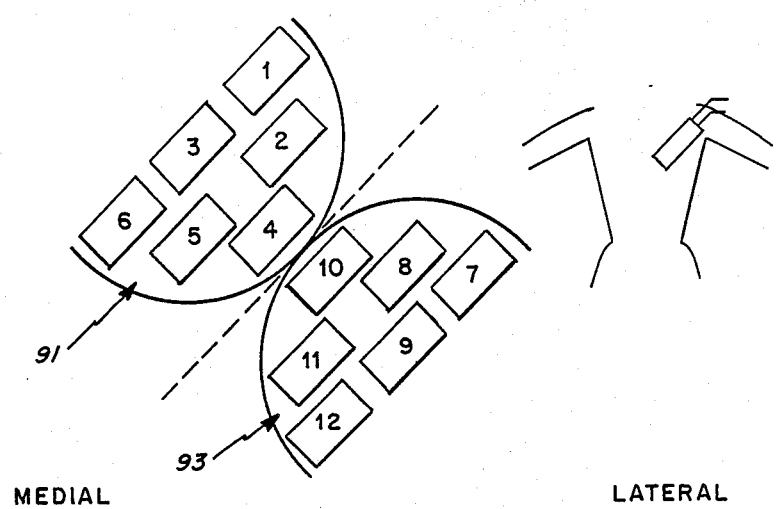
Figure 21B:
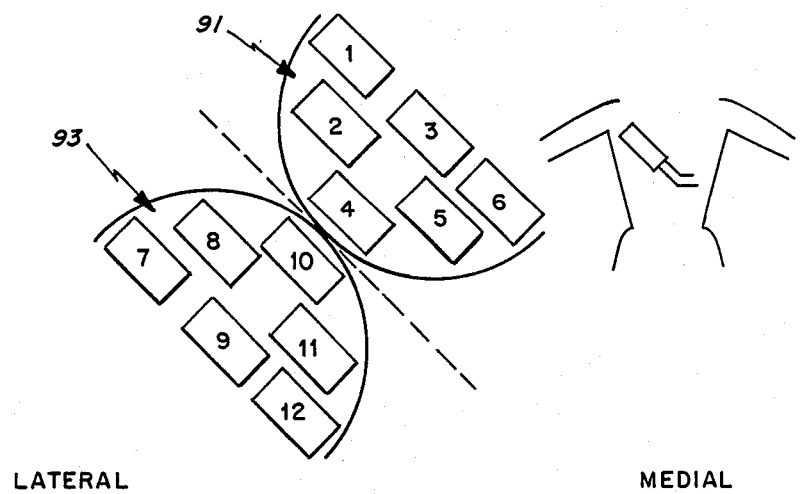
Figure 22A:
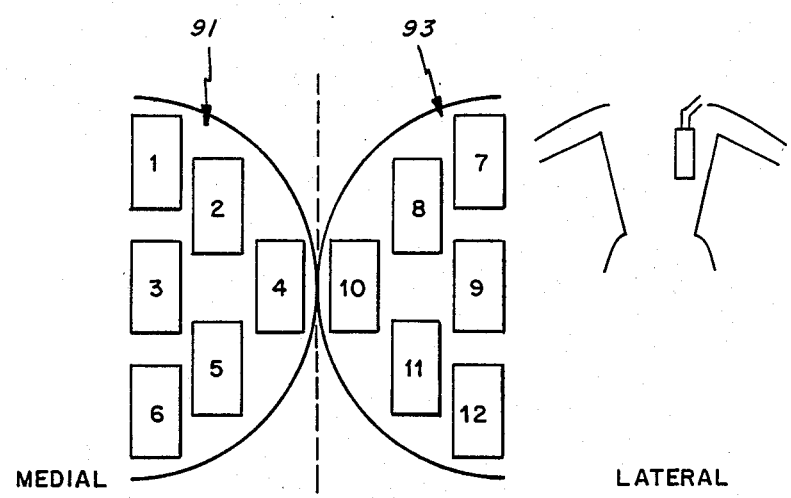
Figure 22B:
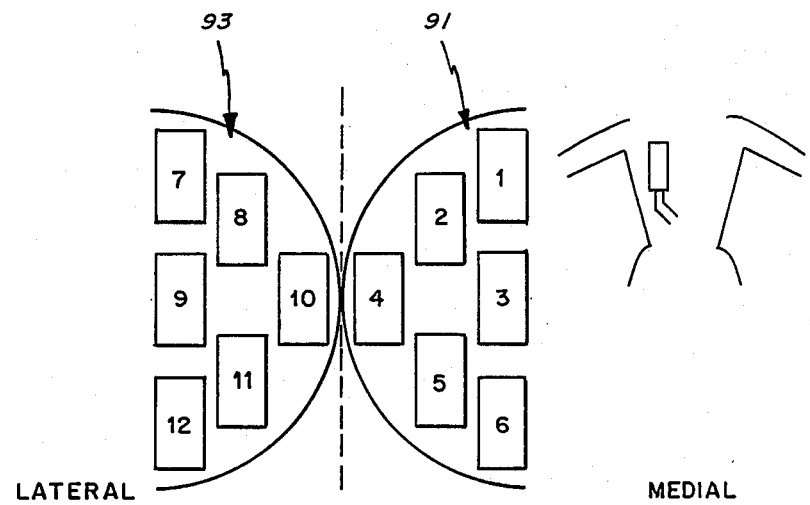

In FIGS. 20A and 20B the position is cranio-caudad. In FIGS. 21A and 21B the pattern is illustrated as oblique. In FIGS. 22A and 22B the pattern is lateral.

It is further to be noted that the compression that has been referred to previously is also believed to lead to tumor enhancement. An elevated temperature is generally associated with the tumor due to the metabolic activity of the tumor. The cells are consuming energy and thus generate heat. In a cancerous tumor the cells double faster and thus are more active and generate more heat. Also, the tumor has generally poor vascularity and thus cannot dump the heat that good. Thus, when the blood circulating about the tumor is also compressed this reduces the temperature of the surrounding tissue with respect to the tumor tissue. This thus tends to enhance the temperature differential between the tumor itself and the surrounding temperature.

As indicated previously, it is desired to compare the like or common location between each breast to determine a temperature differential therebetween. It is also desired to have the capability of making a comparison between a particular temperature at an antenna location for comparison with the average breast temperature. There is a possibility of cold spots in the breast and thus it is preferred to average the temperature throughout the breast and then make the comparison of the average with each individual reading.

Figure 23A:
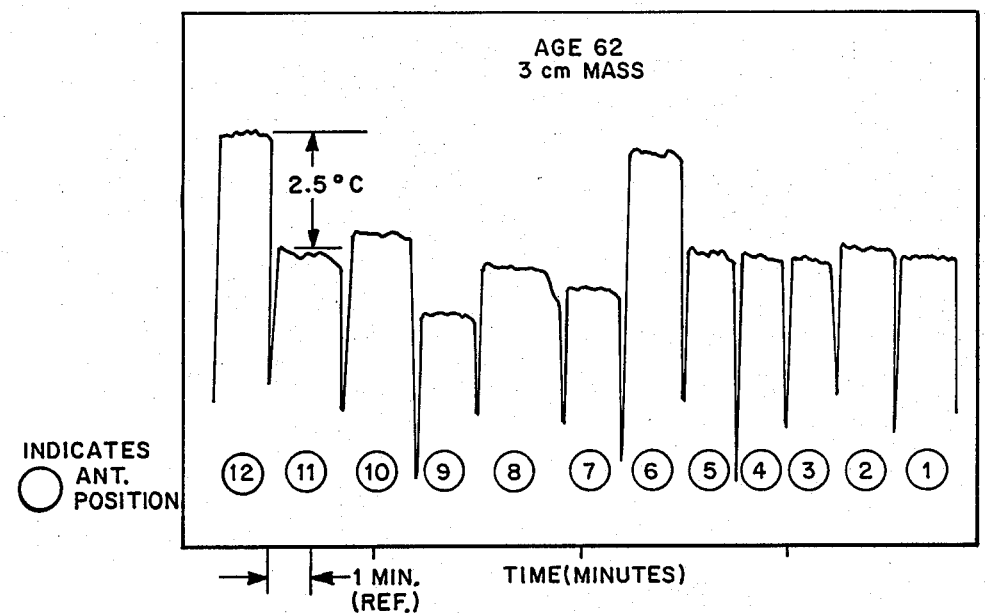
FIGS. 23A and 23B illustrate a microwave thermogram and associated temperature plot for the single housing antenna pattern.
Figure 23B:
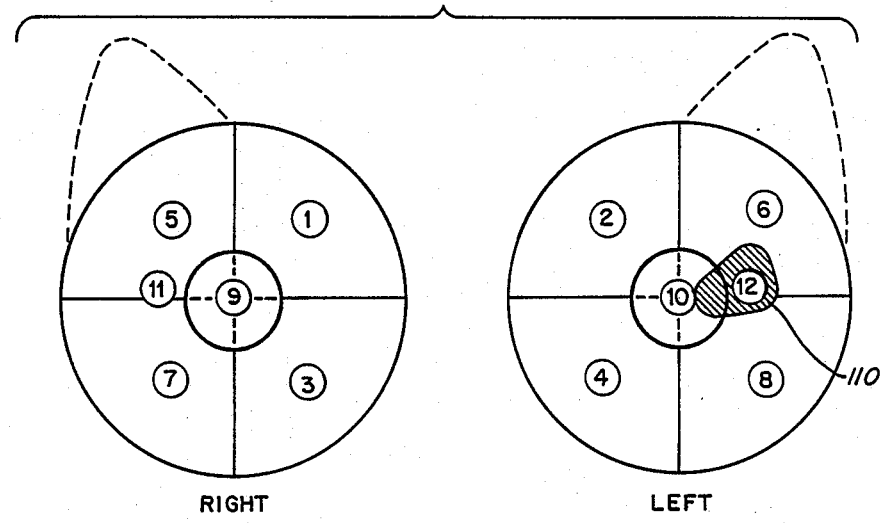

Reference is now made to FIG. 23A which shows a microwave thermogram. This is in association with the embodiment of the invention employing five antennae illustrated at the left breast as antennae #2, #4, #6, #8, #10 and #12. Associated with the right breast are antennae #1, #3, #5, #7, #9 and #11. Also shown this plot indicating temperature associated with each of the four numbered antennae. Also illustrated in FIGS. 23A and 23B is a site 110 where a tumor exists. With reference to the drawing it noted that, for example, a comparison of common points #1 and #2 indicates little or no temperature differential. The same also applies to a comparison between common points #3 and #4. Now, a comparison between common points #5 and #6 indicates a temperature differential. A temperature differential is also indicated between common points #9 and #10. However, note that the maximum temperature differential is detected at the antenna #12 where the temperature differential between #11 and #12 is on the order of 2.5° C.

Again, in FIG. 23A direct comparisons of common point for common point are made. However, in an alternate embodiment of the invention each of the antenna sites may be compared with a common average. This is desired because a temperature differential does not necessarily indicate a tumor if there is a cold spot. It may simply indicate that there is an elevated temperature of good tissue in comparison with the cold spot. Therefore, by averaging all of the breast temperatures this should eliminate all of the problems associated with detection of cold spots.

As indicated previously, by compressing the breast, one reduces the tissue thickness. This is particularly helpful in connection with the measurement of large breasts in which there may be difficulty obtaining proper measurements by surface contact without compression. It is also noted that with the double antenna arrangement, one is measuring from opposing surfaces. This allows determination of depth, which again is particularly helpful in larger breasts, although it also applies to all breasts. For example, if a tumor is located midway between the two opposing antennae of a particular breast, the signal strength is approximately equal at both antennae. However, if the tumor is offset, the degree of offset can be determined by the signal strength at the two opposed antennae. By way of example, refer to FIGS. 17A and 17B and the arrays 41 and 51. At the same breast, like opposed antennae positions may be sensed to determine the position of tumor therebetween. Furthermore, by using opposed antenna arrays, this means that either side of a particular breast can be examined with a reduced path length by a factor of 2, because one is looking from two opposing surfaces.

Figure 24:
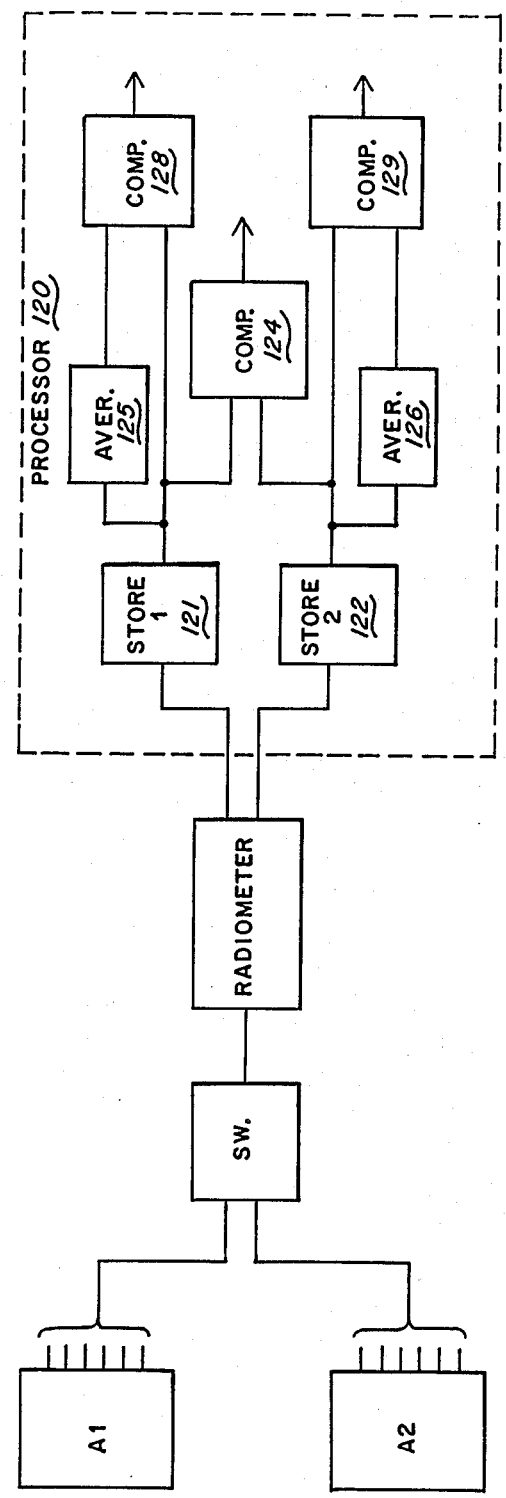
FIG. 24 is a circuit diagram associated with the control electronics associated with temperature measurement.

FIG. 24 is a schematic diagram illustrating some of the electronics that may be employed in providing some of the comparisons previously referred to. In FIG. 24 there are shown the arrays A1 and A2 each of which have multiple antennae coupling to the processor 120. It is noted that the arrays A1 and A2 couple to a multiplexing switch 119 of conventional design. The output of the switch 119 couples to the radiometer R and the output of the radiometer couples to the stores 121 and 122. The radiometer R detects the respective temperature signals from the antennae and the processor 120 records these signals for subsequent processing.

The processor 120 may be a computer that has certain inputs coupled thereto by a keyboard for indicating whether one or the other breast is being examined. Thus, for example, if it is assumed that the left breast is being examined then a particular pattern of storage occurs in devices 121 and 122 so as to provide points on the left breast that can be compared. When the right breast is then compared like signals will be coupled to store 121 and 122 for the sake of discussion herein store #1 in FIG. 24 may be considered as being associated with the left breast while store #2 is associated with the right breast.

In FIG. 24 there is shown one comparator 124. It simply receives signals from each of the stores 121 and 122 for making a direct comparison which is the comparison illustrated in FIG. 23 between common points on each breast. Also illustrated in FIG. 24 is an averaging circuit 125 and a second averaging circuit 126. The averaging circuits take all of the locations associated with the left breast and average them and the averaging circuit 126 takes all locations associated with the right breast and averages them. Also illustrated in FIG. 24 are two other comparators 128 and 129. The comparator 128 compares the average with readings from the left breast and the comparator 129 compares the average with readings from the right breast. A further comparator may be used to compare the outputs from the comparators 128 and 129.

Again, in summary it is desired to make comparisons between common points on each breast. This may be made on a direct comparison basis but preferably is made by comparing the reading from an antenna with average breast temperature, for example, the comparator 128 can provide such a reading.

In the mammography it is possible to detect the tumor mass and also the contrast with respect to surrounding tissue. Mammography defines the location, size and structure of a tumor. On the other hand with regard to the use of microwave energy for detection, what can be detected is actual thermal activity generally independent of size of the tumor. It is expected that this detection of thermal activity actually precedes the formation of mass and thus may give an early indication of the intended growth of a cancerous tumor. It is also noted that the antenna placements in accordance with the invention are preferably provided so that comparisons can be made between detections in accordance with the present invention and detections can be made by the presently used mammography techniques.

Having now described a limited number of embodiments of the present invention, it should now be apparent to those skilled in the art that numerous other embodiments and modifications thereof are contemplated as falling within the scope of the present invention as defined by the appended claims. For example, there is described herein, antennae in the form of waveguide members. These antennae can be air filled as well as dielectrically filled. They may be provided with only a dielectric window at the end of the waveguide. Furthermore, the waveguide type antenna may be replaced by a printed antenna construction.

What is claimed is:

1. Microwave breast tumor detection apparatus comprising;
   a plurality of microwave receiving antennae,
   means for supporting said receiving antennae in opposed array conforming substantially in size to the breast being screened,
   means coupled from said receiving antenna arrays for detecting temperature readings corresponding respectively to the breast temperature at sites underlying the receiving antennae,
   said means for supporting including separately disposed housings for supporting the respective opposed arrays,
   and means associated with said antenna supporting means for compressing the breast between said opposed arrays so as to reduce tissue thickness being examined.

2. Microwave breast tumor detection apparatus as set forth in claim 1 wherein said means for supporting said receiving antennae includes at least one housing having a cupped surface at which the antennae are supported.

3. Microwave breast tumor detection apparatus as set forth in claim 2 wherein said antenna array is substantially symmetric so as to provide relatively uniform breast coverage.

4. Microwave breast tumor detection apparatus as set forth in claim 3 wherein the antennae of the array number on the order of six antennae.

5. Microwave breast tumor detection apparatus as set forth in claim 3 wherein each antenna has a domed end at said housing cupped surface so as to prevent air pockets between the housing and breast.

6. Microwave breast tumor detection apparatus as set forth in claim 3 wherein each antenna comprises a dielectrically-filled waveguide section.

7. Microwave breast tumor detection apparatus as set forth in claim 3 wherein said means for compressing includes a gripping bar associated with said housing.

8. Microwave breast tumor detection apparatus as set forth in claim 7 wherein said cupped surface is supported substantially vertically.

9. Microwave breast tumor detection apparatus as set forth in claim 1 further including means commonly intercoupling said separately disposed housings to provide disposition of said opposed arrays in contacting breast position at respective opposite sides of the breast being screened, and means for compressing the breast between the housings including means for moving the housings together to compress the breast so as to reduce tissue thickness to thereby reduce blood circulation in the breast thus reducing the temperature of the tissue surrounding the tumor in comparison to the tumor temperature to thus enhance the temperature differential between the tumor site and surrounding tissue.

10. Microwave breast tumor detection apparatus as set forth in claim 9 wherein said means for supporting said antennae includes first and second housings each having a cupped surface at which the first and second sets of antennae are supported, respectively.

11. Microwave breast tumor detection apparatus as set forth in claim 10 including means for commonly carrying said first and second housings with associated cupped surfaces disposed in facing relative relationship.

12. Microwave breast tumor detection apparatus as set forth in claim 11 wherein said means for commonly carrying includes a support member means for supporting the first housing substantially horizontal and in fixed position.

13. Microwave breast tumor detection apparatus as set forth in claim 12 including means for supporting the second housing over the first housing from said support member means.

14. Microwave breast tumor detection apparatus as set forth in claim 13 wherein said means for compressing includes a carriage on said support member means and means for operating said carriage to bring the second housing toward the first housing to compress the breast therebetween.

15. Microwave breast tumor detection apparatus as set forth in claim 14 including means for providing pivotal adjustment and positioning of the second housing so that the second housing is displaced further from the first housing at a point remote from the support member means than at a point adjacent the support member means.

16. Microwave breast tumor detection apparatus as set forth in claim 15 including means for locking the second housing in an angular tilted position relative to the first housing.

17. Microwave breast tumor detection apparatus as set forth in claim 10 wherein each antenna array is substantially symmetric so as to provide relatively uniform breast coverage.

18. Microwave breast tumor detection apparatus as set forth in claim 17 wherein each antenna has a domed end at said housing cupped surface so as to prevent air pockets between the antenna and the breast.

19. Microwave breast tumor detection apparatus as set forth in claim 1 including means for averaging all breast temperatures and means for comparing each individual antenna temperature with the average.

20. Microwave breast tumor detection apparatus as set forth in claim 10 including means for comparing the temperature from like sites of each breast to detect a differential temperature therebetween.

21. A method for the detection of a cancerous tumor comprising the steps of, providing a plurality of microwave receiving antennae, supporting these antennae in opposed arrays conforming substantially in size to the breast being screened, supporting the opposed arrays in respective support members, compressing the breast between said support members so as to reduce tissue thickness that is being examined, and detecting the temperature readings with the breast compressed corresponding, respectively, to the breast temperature at sites underlying the receiving antennae.

22. A method as set forth in claim 21 including providing supported in an upper position and the other in a lower position so as to provide separate upper and lower antenna arrays with the breast being compressed therebetween.

23. A method as set forth in claim 22 wherein the breast is compressed only with sufficient force to provide coverage of all antennae of the array.

24. A method as set forth in claim 23 including comparing temperature readings from common locations on each breast.

25. A method as set forth in claim 23 including averaging breast temperature and comparing each individual antenna temperature with the average.

26. A method as set forth in claim 21 including providing the opposed arrays as facing arrays supported on either side of the breast with the breast being compressed therebetween and comparing signal strength from oppositely disposed antennae of each array to determine tumor depth therebetween.

27. A microwave breast tumor detection apparatus comprising:
a first plurality of microwave receiving antennae,
a first housing supporting said first plurality of microwave receiving antennae in a first array conforming substantially in size to the breast being screened,
a second plurality of microwave receiving antennae,
a second housing supporting said second plurality of microwave receiving antennae in a second array conforming substantially in size to said first array,
means coupled from said receiving antenna arrays for detecting temperature readings corresponding respectively to the breast temperature at sites underlying the receiving antennae,
and means commonly intercoupling said first and second housings to provide disposition of said first and second antenna arrays in contacting breast position at respective opposite sides of the breast being screened and including means for moving the housings together to compress the breast so as to reduce tissue thickness to thereby reduce blood circulation in the breast thus reducing the temperature of the tissue surrounding the tumor in comparison to the tumor temperature to thus enhance the temperature differential between the tumor site and surrounding tissue.

28. A microwave breast tumor detection apparatus as set forth in claim 27 wherein said means for detecting includes separate means for obtaining temperature readings of subcutaneous temperature from oppositely disposed breast surface sites.

29. A microwave breast tumor detection apparatus as set forth in claim 28 wherein said first and second plurality of microwave receiving antennae are equal in number so as to provide matching sites from both sides of the breast being screened.

30. A microwave breast tumor detection apparatus as set forth in claim 29 including means for comparing signal strength from oppositely disposed antennae of each array to determine tumor depth therebetween.

31. A method of detecting a breast tumor comprising the steps of, providing a first plurality of microwave receiving antenna, supporting the first plurality of microwaves receiving antennae and a first array conforming substantially in size to the breast being screened, providing a second plurality of microwave receiving antennae, supporting the second plurality of microwave receiving antennae and a second array conforming substantially in size to said first array, detecting temperature readings corresponding respectively to the breast temperature at sites underlying the receiving antennae, disposing the first and second antennae arrays in contacting breast position at respective opposite sides of the breast being screened and moving the housings together to compress the breast so as to reduce tissue thickness to thereby reduce blood circulation in the breast thus reducing the temperature of the tissue surrounding the tumor in comparison to the tumor temperature to thus enhance the temperature differential between the tumor site and surrounding tissue.

* * * * *

UNITED STATES PATENT AND TRADEMARK OFFICE
CERTIFICATE OF CORRECTION

PATENT NO. : 4,774,961

DATED : Oct. 4, 1988

INVENTOR(S) : Carr

It is certified that error appears in the above-identified patent and that said Letters Patent is hereby corrected as shown below:

Title page, Item [75]   Inventor:

"Kenneth A. Carr" should read --Kenneth L. Carr--.

Signed and Sealed this

Twenty-third Day of January, 1990

Attest:

JEFFREY M. SAMUELS

Attesting Officer          Acting Commissioner of Patents and Trademarks